United States Patent
Jew et al.

(10) Patent No.: US 12,076,133 B1
(45) Date of Patent: Sep. 3, 2024

(54) SIGNATURE MITIGATION FOR UNCOOLED THERMAL SYSTEMS

(71) Applicant: BAE Systems Information and Electronic Systems Integration Inc., Nashua, NH (US)

(72) Inventors: Jeffrey L. Jew, Brookline, NH (US); Michael A. Costolo, Amherst, NH (US); Adam O. Powers, Manchester, NH (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 465 days.

(21) Appl. No.: 17/217,288

(22) Filed: Mar. 30, 2021

(51) Int. Cl.
| | |
|---|---|
| *A61B 5/11* | (2006.01) |
| *A61B 5/00* | (2006.01) |
| *A61B 5/113* | (2006.01) |
| *A61B 5/349* | (2021.01) |
| *A61N 1/39* | (2006.01) |

(Continued)

(52) U.S. Cl.
CPC .......... *A61B 5/1114* (2013.01); *A61B 5/0024* (2013.01); *A61B 5/1117* (2013.01); *A61B 5/113* (2013.01); *A61B 5/349* (2021.01); *A61B 5/4094* (2013.01); *A61N 1/3925* (2013.01); *G01J 5/0804* (2022.01); *G01J 5/0813* (2022.01); *H04N 23/23* (2023.01); *H04N 25/21* (2023.01); *A61B 2562/0219* (2013.01); *G01J 2005/0077* (2013.01)

(58) Field of Classification Search
CPC ... A61B 5/0024; A61B 5/1114; A61B 5/1117; A61B 5/113; A61B 5/349; A61B 5/4094; A61B 2562/0219; A61N 1/3925; G01J 5/0804; G01J 5/0813; G01J 2005/0077; H04N 23/23; H04N 25/21
See application file for complete search history.

(56) References Cited

U.S. PATENT DOCUMENTS

| | | | |
|---|---|---|---|
| 5,420,419 A | * | 5/1995 | Wood .................... H04N 5/33 250/370.15 |
| 7,154,599 B2 | | 12/2006 | Adams et al. |

(Continued)

FOREIGN PATENT DOCUMENTS

| | | |
|---|---|---|
| JP | 3646164 B2 | 5/2005 |
| KR | 101392721 B1 | 5/2014 |

OTHER PUBLICATIONS

Boston Electronics, Ultraviolet Photodiodes—SIC, published by at least May 24, 2020—see WayBack Machine Capture, available at http://www.boselec.com/product-category/ultraviolet-photodiodes-sic (Year: 2020).

(Continued)

*Primary Examiner* — Mark R Gaworecki
(74) *Attorney, Agent, or Firm* — Scully Scott Murphy & Presser PC; Gary McFaline

(57) ABSTRACT

Techniques for reducing a likelihood of detection of an imaging system by another imaging system are provided. For example, a mechanism may be used to interrupt an optical path between pulse biased thermal sensors and an aperture of the system when the pulsed biased thermal sensors are pulse biased. For example, emissions may be directed to a beam dump. Other techniques may include a mechanism for linearly moving the thermal sensor array or rotating a mirror.

10 Claims, 37 Drawing Sheets

(51) Int. Cl.
*G01J 5/08* (2022.01)
*G01J 5/0804* (2022.01)
*G01J 5/0813* (2022.01)
*H04N 23/23* (2023.01)
*H04N 25/21* (2023.01)
*G01J 5/00* (2022.01)

(56) References Cited

U.S. PATENT DOCUMENTS

| | | |
|---|---|---|
| 10,348,982 B1 | 7/2019 | Lacroix |
| 11,368,637 B1 | 6/2022 | Tremblay et al. |
| 11,438,529 B1 | 9/2022 | Jew et al. |
| 11,652,955 B1 | 5/2023 | Jew et al. |
| 2003/0213910 A1* | 11/2003 | Anderson ............... H04N 5/33 250/338.1 |
| 2012/0169053 A1 | 7/2012 | Tchoryk, Jr. et al. |
| 2012/0235042 A1 | 9/2012 | Cole et al. |

OTHER PUBLICATIONS

Hamamatsu Photonics, Si Photodiodes: UV to near IR radiation, Selection Guide, Apr. 2020, available at https:// www.hamamatsu. com/content/dam/hamamatsu-photonics/sites/documents/99_SALES_ LI B RARY/ssd/si_pd_kspd000 1e. pdf (Year: 2020).

\* cited by examiner

Correspondence Table
800

| Row of Pixels | Mirrors |
|---|---|
| AAA | ZZZ |
| BBB | YYY |

Fig. 8

Correspondence Table 1300

| Shaft Position | Row of Pixels |
|---|---|
| 111 | MMM |
| 222 | NNN |

Fig. 13

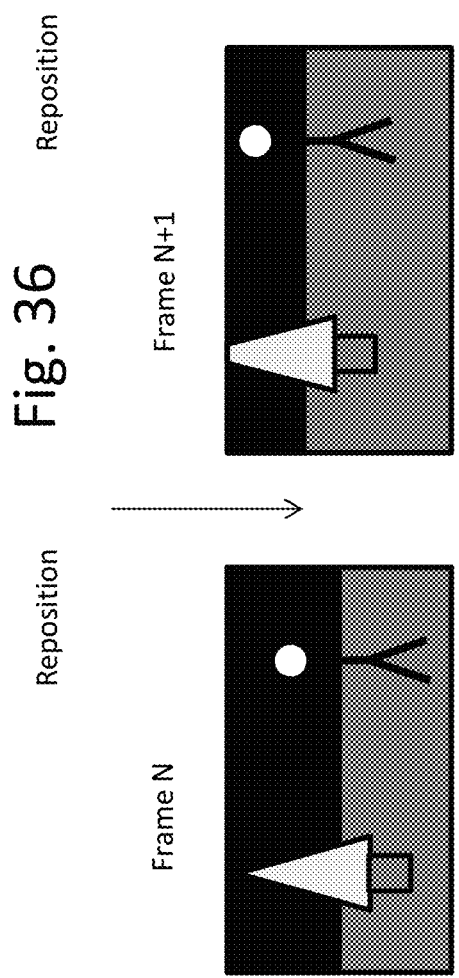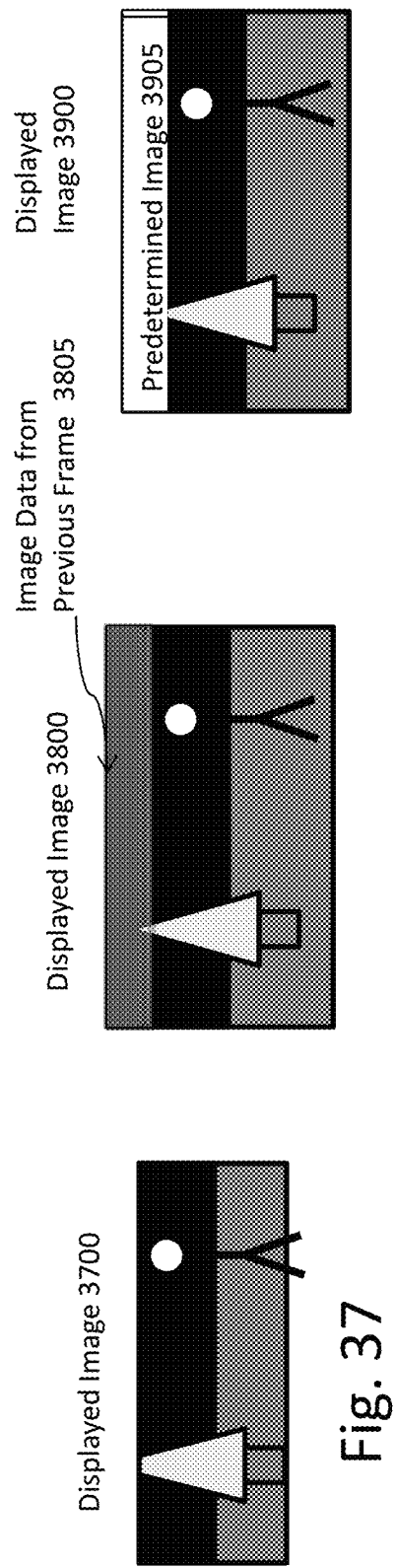

SIGNATURE MITIGATION FOR UNCOOLED THERMAL SYSTEMS

FIELD OF THE DISCLOSURE

This disclosure relates to imaging systems. This disclosure also relates to mechanisms and techniques to reduce a likelihood of detection of the imaging system by another imaging system.

BACKGROUND

Typical imagers are constructed from an array of sensors, such as microbolometers. An optical system focuses incident light in an image on the array. The microbolometers are designed to be highly absorptive in the spectral band of interest. As the microbolometers absorb the optical energy their temperature rises. This temperature is measured by the bolometric effect, wherein the resistance of the microbolometer is a function of its temperature. The most common bolometric material is vanadium oxide which has high bolometric coefficients (delta-R/delta-T) but a low device resistance. To compensate for this low resistance, arrays use a "pulse bias" readout where the microbolometer is allowed to thermally equilibrate over several milliseconds and the resistance is read using a voltage or current pulse. System performance of these pulse biased microbolometers is optimized through efficient and well-focused optics, highly absorptive material, and thermally-isolated detectors.

However, these types of imagers may be detected by another imager, e.g., another imaging system. For example, U.S. application Ser. No. 16/987,879 describes a detector and an imaging system for detecting microbolometers.

SUMMARY

Accordingly, disclosed are mechanisms and techniques for reducing a likelihood of detection of an imaging system by another imaging system.

In an aspect of the disclosure, the system may comprise a focal-plane array (FPA) which may comprise a two-dimensional configuration of thermal sensors arranged in rows and columns; and readout circuitry to pulse bias one or more thermal sensors of one or more selected rows and obtain output from the pulse biased thermal sensors. The system may further comprise a shutter and a processor configured to control the shutter to interrupt an optical path between the pulse biased thermal sensors and an aperture of the system while the pulsed biased thermal sensors are being pulse biased.

In an aspect of the disclosure, the system may further comprise at least one focusing lens and relay optics. At least a portion of the shutter may be positioned at an intermediate focal plane.

In an aspect of the disclosure, the shutter may comprise a plurality of alternating transparent and opaque sections coupled to a shaft and a motor. The processor may control the position of these sections relative to the pulsed biased thermal sensors using the motor.

In an aspect of the disclosure, the system may further comprise an encoder configured to provide a location of the shaft to the processor. The processor may transmit a line synchronization signal to the readout circuitry based on the position of the shaft.

In an aspect of the disclosure, the system may further comprise a memory that has a correspondence table. The correspondence table associates the position of the shaft with a row of pixels for readout. The processor determines the one or more selected row of pixels for readout using the correspondence table and the detected position.

In other aspects of the disclosure, the shutter may comprise a digital micromirror device (DMD).

In an aspect of the disclosure, the processor may be configured to an angle of mirrors of the DMD to interrupt the optical path between the pulse biased thermal sensors and the aperture of the system while the pulsed biased thermal sensors are pulse biased.

In an aspect of the disclosure, the system may further comprise a beam dump and while the pulsed biased thermal sensors are pulse biased, corresponding mirrors of the DMD may be rotated such that emissions are reflected toward the beam dump.

In an aspect of the disclosure, the beam dump may be a portion of the housing of the system.

In an aspect of the disclosure, the beam dump may be made of an absorptive material. In an aspect of the disclosure, the system further comprises a memory having a correspondence table associating thermal sensors and corresponding mirrors, respectively, of the DMD. In an aspect of the disclosure, the processor determined which mirrors to rotate based on one or more selected rows of pixels and one or more thermal sensors for pulse biasing and the correspondence table.

Also disclosed is a system comprising at least one focusing lens, a mirror, a focal plane array and a processor. The focal plane array may comprise a two-dimensional configuration of thermal sensors arranged in rows and columns; and readout circuitry to pulse bias one or more thermal sensors of one or more selected rows, and obtain output from the pulse biased sensors. The processor may be configured to generate an image for each frame of a plurality of frame, each frame comprising the one or more selected rows. The mirror may be rotatable. The processor may be configured to generate the image based on the angle of the mirror.

In an aspect of the disclosure, the system may further comprise a motorized mirror shaft; and a motor controller configured to rotate the motorized mirror shaft changing an angle of the mirror. The change in angle of the mirror may cause a linear displacement of light at the two-dimensional configuration of thermal sensors. In this aspect, the processor may be configured to control the motor controller to rotate the motorized mirror shaft and receive motor position information.

In an aspect of the disclosure, the processor may be configured to generate the image for each frame based on the received motor position information and readout data from the pulse biased thermal sensors for a respective frame.

In an aspect of the disclosure, the processor may be configured to cause of the motor controller to change the angle of the mirror between pulse biasing for different frames.

In an aspect of the disclosure, the system may further comprise a vibration isolator and an encoder. In this aspect, the mirror may be in contacted with a free end of the vibration isolator. A change in angle of the mirror may cause a linear displacement of light at the two-dimensional thermal sensors. The encoder may be configured to detect an angular position and the processor may be configured to receive the angular position and generate the image for each frame based on the received angular position and readout data from pulsed biased thermal sensors for a respective frame.

Also disclosed is a system comprising at least one focusing lens, a focal plane array and a processor. The focal plane array may comprise a two-dimensional configuration of thermal sensors arranged in rows and columns; and readout circuitry to pulse bias one or more thermal sensors of one or more selected rows, and obtain output from the pulse biased sensors. The processor may be configured to generate an image for each frame of a plurality of frame, each frame comprising the one or more selected rows. The two-dimensional configuration of thermal sensors may be disposed on a moveable stage. The processor may be configured to generate the image based on the position of the moveable stage.

In an aspect of the disclosure, the system may further comprise a vibration isolator and an encoder. A free end of the vibration isolator may be in contact with the moveable stage. The moveable stage may be linearly moveable. The encoder may be configured to detect linear position of the moveable stage. The processor may be configured to receive the linear position and generate the image for each frame based on the received linear position and readout data from the pulsed biased thermal sensors for a respective frame.

In an aspect of the disclosure, the system may further comprise a motorized frame as the moveable stage and a motor controller. The two-dimensional configuration of thermal sensors may be mounted to the motorized frame. The motor controller may be configured to linearly move the motorized frame. The processor may be configured to control the motor controller to linearly move the motorized frame and receive position information.

In an aspect of the disclosure, the processor may be configured to generate the image for each frame based on the received position information and readout data from pulsed biased thermal sensors for a respective frame.

In an aspect of the disclosure, the processor may be configured to cause of the motor controller to change the linear position of the motorized frame between pulse biasing different frames or rows.

BRIEF DESCRIPTION OF THE DRAWINGS

FIG. 8 depicts a correspondence table of rows of pixels and mirrors in the DMD in accordance with aspects of the disclosure;

FIG. 13 depicts another correspondence table in accordance with aspects of the disclosure of the shaft position associated with the rows of pixels;

FIG. 36 depicts an example of image data of three frames in accordance with aspects of the disclosure; and FIGS. 37-39 depict examples of displayed images in accordance with aspects of the disclosure.

DETAILED DESCRIPTION

Figure 1:
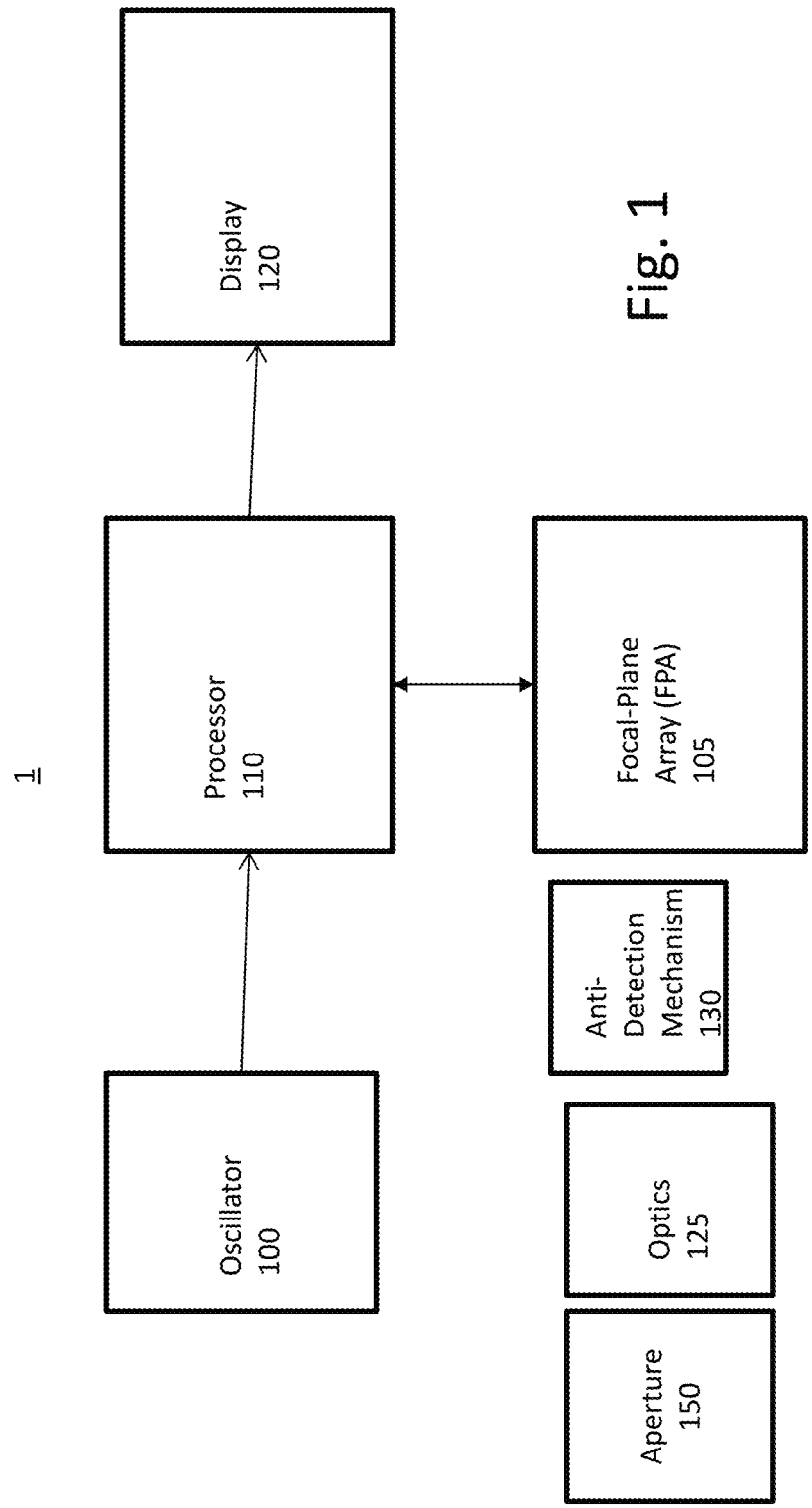
FIG. 1 depicts an system in accordance with an aspect of the disclosure.

FIG. 1 depicts an imaging system 1 in accordance with aspects of the disclosure. The image system 1 senses radiation such as infrared radiation to generate a thermal image.

The imaging system 1 may comprise an oscillator 100. The oscillator 100 may be a crystal oscillator. A crystal oscillator resonates and is capable of producing a precise frequency for use as a precision main clock for the imaging system 1. This main clock is the source of other clock(s) and synchronization signal(s)/command(s) used in the imaging system 1.

The imaging system 1 may also include a processor 110. The processor 110 may be a FPGA. In other aspects of the disclosure, the processor 110 may be a microcontroller or microprocessor or any other processing hardware such as a CPU or GPU. In an aspect of the disclosure, the processor 110 may be configured to execute one or more programs stored in a computer readable storage device. The computer readable storage device can be RAM, persistent storage or removable storage. A storage device is any piece of hardware that is capable of storing information, such as, for example without limitation, data, programs, instructions, program code, and/or other suitable information, either on a temporary basis and/or a permanent basis.

The main clock is feed to the processor 110. Using the main clock, the processor 110 generates other clock(s) and command(s) used by the system. The command(s) and clock(s) are sent to a focal-plane array (FPA) 105.

Figure 2:
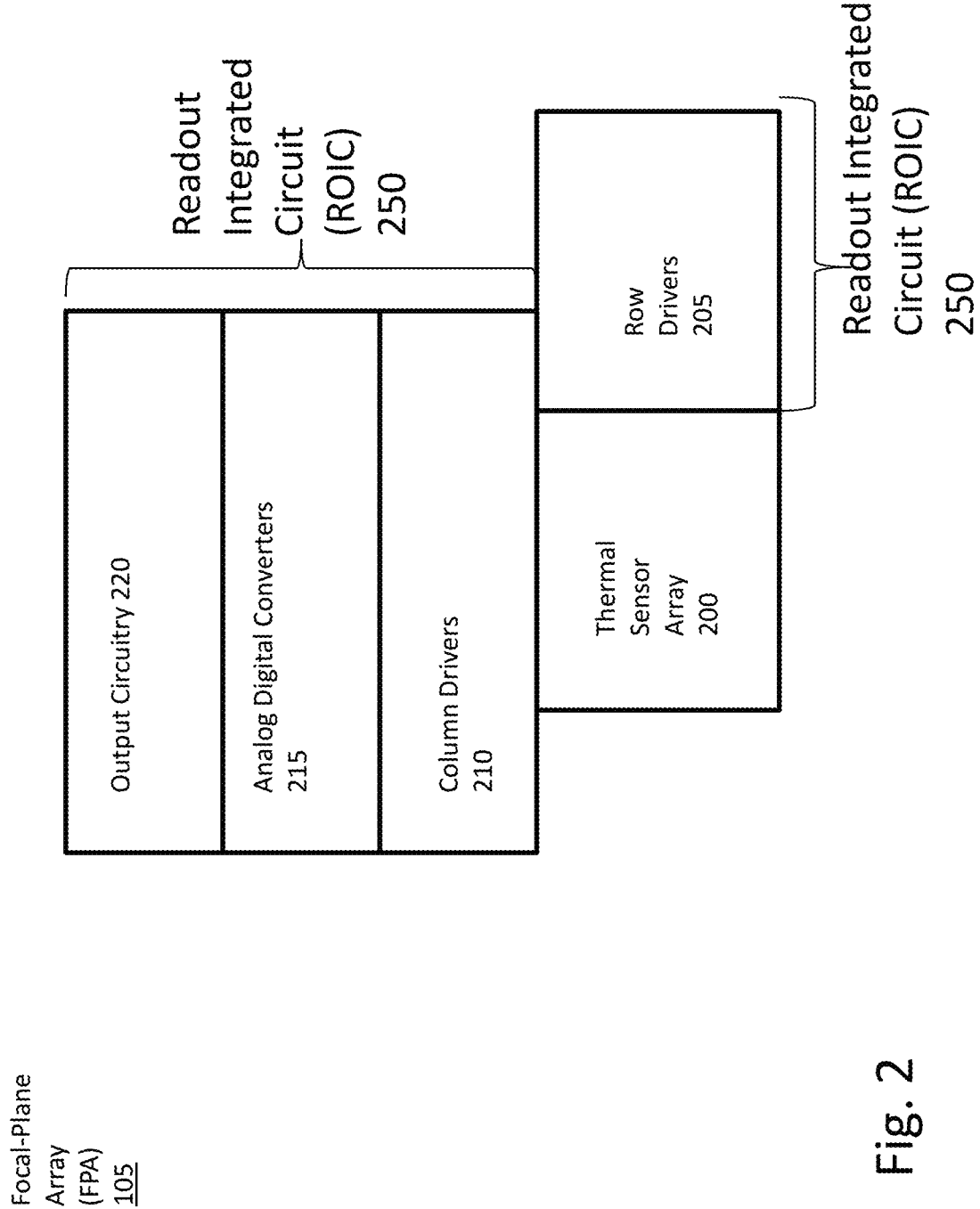
FIG. 2 depicts a focal-plane array in accordance with aspects of the disclosure.

Certain components of the FPA 105 are shown in FIG. 2 (as blocks). The FPA 105 may comprise a readout integrated circuit (ROIC) 250 and a thermal sensor array 200. The thermal sensor array 200 may be responsive to IR radiation. For example, the thermal sensor array 200 may be responsive to mid-wavelength IR. In other aspects, the thermal sensor array 200 may be responsive to long-wavelength IR. In other aspects, the thermal sensor array 200 may be responsive to both mid-wavelength IR and long-wavelength IR. For example, the thermal sensor array 200 may be responsive to wavelengths between 3 µm to 15 µm. In other aspects, the thermal sensor array 200 may be responsive to wavelengths between 6 µm-15 µm. In other aspects, the thermal sensor array 200 may be responsive to wavelengths between 8 µm-12 µm. In other aspects, the thermal sensor array 200 may be responsive to wavelengths between 3 µm-8 µm.

The imaging system 1 may comprise optics 125. The optics 125 may include one or more lens. For example, the lenses may include a focus lens and a relay lens. The lenses may be mounted to a housing (not shown). The housing may have an aperture 150 such as an opening, window, or slit to allow infrared radiation into the imaging system 1. In some aspects, the opening may be covered. The cover may be transmissive for the IR.

The lenses may be a plano-convex lens. The lens may be Zinc Selenide ZnSe. A ZnSe lens is designed for the infrared spectrum. However, in other aspects, other materials may be used.

In some aspects, the lenses may be coated to improve transmission efficiency for a specific range of wavelengths. For example, a broadband anti-reflection (BBAR) coating may be used. The coating may be set for a desired wavelength range.

The size of the lens, number of lens and focal length, may be defined based on a desired size for the imaging system 1. Smaller lens and focal lengths may be used where the system 1 is desired to be small and portable. Larger lens and focal lengths may be used where the system 1 is fixed, such as mounted to a vehicle, such as an airplane, helicopter, boat, truck, bus, motorcycle, submarine, UAV, etc.

The optics 125 may include objective lens 505 (or object lens group 505) and relay optics 510 (relay lens group 510A).

Figure 4:
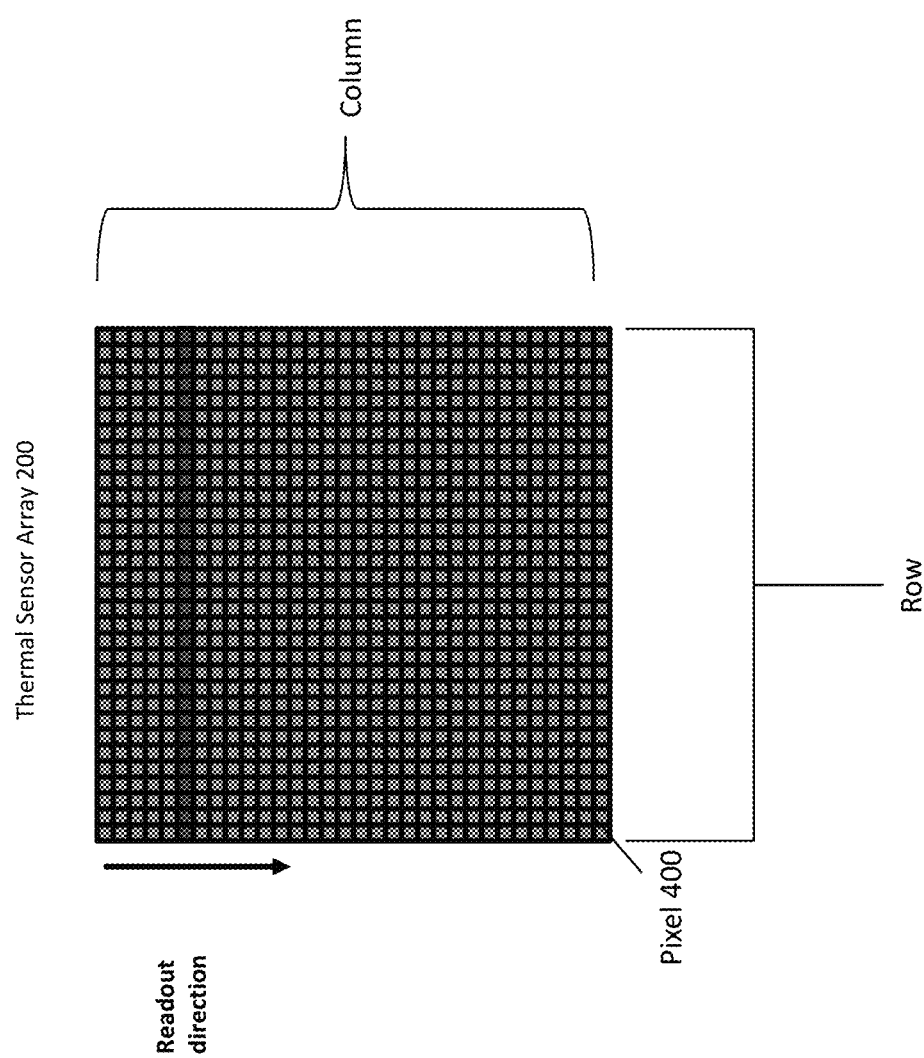
FIG. 4 depicts the thermal sensor array 200 and an example of the readout direction is accordance with aspects of the disclosure.

The thermal sensor array 200 may have a plurality of thermal sensors. The sensors are arranged in rows and columns as shown in FIG. 4. The number of rows and columns may be based on the application for the imaging system 1 and the size of the array 200. In some aspects, the thermal sensor array 200 may be used for a video graphics array (VGA) and have 480 rows and 640 columns. In other aspects of the disclosure, the thermal sensor array 200 may have different resolution. For example, the thermal sensor array 200 may be 160 columns and 120 rows, 320 columns and 240 rows, 1024 columns and 768 rows or 1920 columns and 1200 rows. However, the number of columns and rows are not limited to the above examples and there is no required minimum size or maximum size of the thermal sensor array 200, subject to the design and operation.

In an aspect of the disclosure, each thermal sensor may be formed from IR sensitive material such as vanadium oxide or metal-doped vanadium oxide to detect the incoming IR radiation which is focused on the thermal sensor array 200 (by the optics 125). This material may cover some or most of an exposed surface of a respective pixel. The IR sensitive material, such as vanadium oxide is a conductive material that heats when exposed to IR radiation. This heating causes the resistance of the material to lower due to the thermal coefficient of resistance (TCR). For example, the TCR of vanadium oxide can be around 2%/C. In some embodiments, the TCR of vanadium oxide can be improved through techniques such as metal doping.

The ROIC 250 may comprise row drivers 205 and columns drivers 210. The TCR causes the measured resistance in the sensor to decrease as the sensor heats up (e.g., through absorbing IR radiation). This decrease in resistance can be measured, for example, using row drivers 205 and column drivers 210 to measure the increased current passing through the decreased resistance. Since the current is inversely proportional to the resistance, the measured current provides a way to measure the resistance, and thus the temperature change, in the thermal sensor. From this, the portion of the temperature change due to IR flux can be determined and thus, a value or values representing the IR radiation measured by the thermal sensor can be determined. The process can be repeated across the array 200 until every thermal sensor is measured.

In an aspect of the disclosure, the thermal sensor array 200 may be physically and electrically connected to the ROIC 250, such as through a set of row lines and column lines in the ROIC 250 underneath the thermal sensor array 200. The row drivers 205 may be coupled to the row lines, which in turn may be coupled to the rows of the array 200, respectively, and column drivers 210 may be coupled to the column lines and which in turn may be coupled to the columns of the array 200, respectively.

The FPA 105 may take IR images in frames (e.g., each frame representing one measurement per pixel 400 or thermal sensor). Each thermal sensor corresponds to a single pixel. Each frame constitutes a single instance of the two-dimensional data. Data is sampled by pulse biasing the respective thermal sensors and computing the corresponding incident IR radiation. Data may be organized by lines which represent a single row or column of data and are read out sequentially. FIG. 4 shows an example of the readout direction. However, the readout direction may be reverse. In one aspect of the disclosure one row, multiple adjacent rows, or subset of pixels within a row or adjacent rows may be sequentially biased. As shown in FIG. 4, the sequence is in the same physical order as in the array. For example, row 1, row 2, row 3, etc. . . . may be biased in that order. However, in other aspects, the order may be different from the same physical order.

The pixels in line may be pulse biased and read simultaneously. In FIG. 4 the darker row represents a line of pixels being pulse biased and read simultaneously.

In another aspect of the invention, data may be organized in one or more subsets or clusters which are not adjacent rows and pulse biased and read in an arbitrary order.

The rows of the thermal sensor array 200 are electrically connected to the row drivers 205 through row lines, such as one row driver and row line per row of pixels. Each row driver is configured to bias (pulse bias) the thermal sensors in its corresponding row. Biasing transmits a biasing current through a set of electrodes, such as a common low voltage source coupled to one side (e.g., one electrode) of each thermal sensor. In addition, the columns of the thermal sensor array 200 are electrically connected to the column drivers 210, such as one column driver per column of pixels per row being concurrently or simultaneously biased.

The column drivers 210 are configured to measure the thermal sensors such as by integrating and measuring the current from a separate high voltage source coupled to the other side of each thermal sensor. For example, each column driver can be coupled to one of the thermal sensors being biased, and measures the current transmitted through the thermal sensor during the biasing (or integration) period or cycle. The measured current represents an analog IR signal.

The timing in which the ROIC 250 begins the pulse biasing for a frame is determined by a frame synchronization command received from the processor 110. Additionally, the row and timing that a specific row is pulse biased is also determined by a line synchronization command received from the processor 110.

Figure 5:
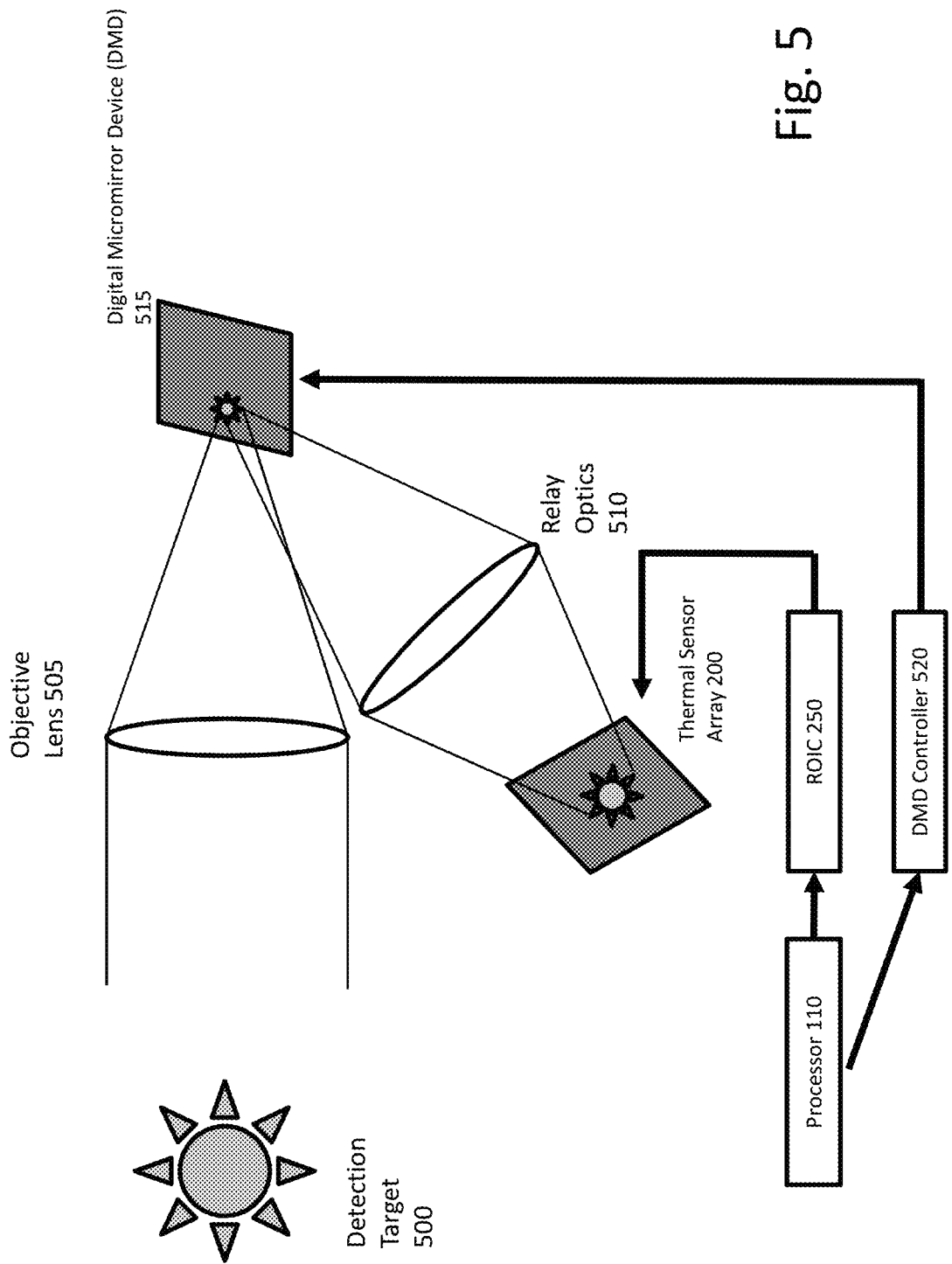
FIG. 5 depicts anti-detection mechanism in the system in accordance with aspects of the disclosure using a digital micromirror device (DMD).

The pulse biasing itself may produce a detectable signature which exits the housing through aperture 150, e.g., thermal energy, by another thermal imaging system. Thus, in accordance with aspects of the disclosure, the system 1 has an anti-detection mechanism 130. In some aspects of the disclosure, the anti-detection mechanism 130 blocks (interrupts) the optical path between the pulse biased thermal sensor and aperture 150 while readout occurs, such as using a shutter (shown in FIGS. 5-7 as a digital micromirror DMD 515 and beam dump 605) or a roller shutter 1000 (shown in FIGS. 10-12).

In accordance with aspects of the disclosure the anti-detection mechanism 130 in controlled in conjunction with the ROIC 250.

The ROIC 250 may be controlled via synchronization commands. For example, the processor 110 may generate the frame synchronization command from the main clock. In an aspect of the disclosure, the processor 110 implements a state machine to generate the frame synchronization command. The frame synchronization command may be an integer multiple of the main clock. The processor 110 also generates the line synchronization command and pixel clock from the main clock.

Figure 3:
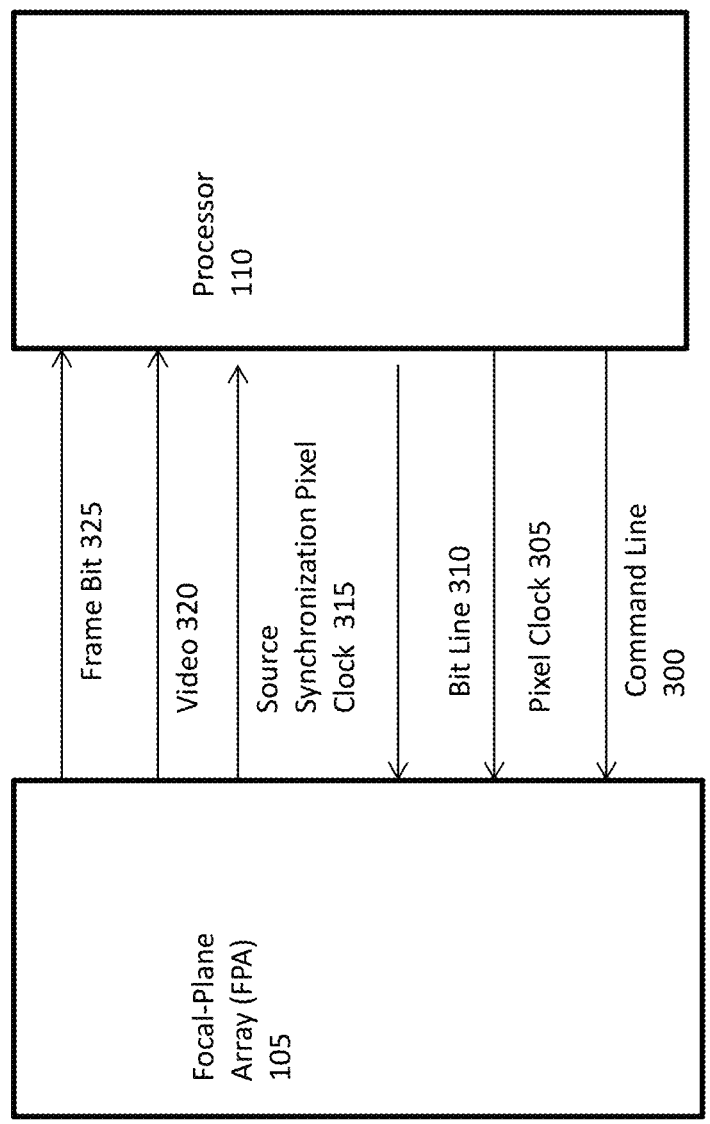
FIG. 3 depicts communication lines between the FPA and a processor in accordance with aspects of the disclosure.

FIG. 3 depicts the communication lines (bus) between the FPA 105 and the processor 110. The frame synchronization commands and line synchronization commands are transmitted from the processor 110 to the FPA 105 via the command lines 300. The pixel clock is transmitted from the processor 110 to the FPA 105 via the pixel clock line 305. Data associated with a command is transmitted from the processor 110 to the FPA 105 via a bit line 310. For example, the specific row that the line synchronization command is for is transmitted via the bit line 310. Further, offset currents for a row may be transmitted via the bit line 310 (associated with an offset current command).

The FPA 105 transmits to the processor 110 a source synchronization clock via line 315. The source synchronization clock is the same as the pixel clock received from the processor 110. The source synchronization clock is used by the processor 110 to confirm the pixel data. For example, there may be a delay associated with routing the clock throughout the system which may vary based on operating voltage, timing frequency, or specific unit number. To account for this delay the source synchronization clock is fed back with the data to avoid issues with data setup and hold. This prevents the processor 110 from sampling the data before the digital signals are stable. The image data, per row, is transmitted from the FPA 105 to the processor 110, for further processing, via the video line 320. Additionally, the FPA 105 transmits to the processor 110 a frame bit via line 325. The frame bit includes which row the image data is for such that the processor 110 can reconstruct the image for the frame.

The pulse biasing may introduce inaccuracies into the measured IR signal currents because the biasing itself may heat the IR sensors, which may cause change in the resistances that is not due to the incoming IR flux being measured. This heating, when measuring the IR sensor, may be the dominant portion of the increased heat which might cause a false detection.

Further, there may be other source of inaccuracies. For example, another source of inaccuracies may be the absolute readings of the IR sensors, which can vary dramatically from sensor to sensor due to factors such as normal fabrication variance (which increases significantly with smaller and thinner sensor design). To address inaccuracies such as these, offset currents can be generated for each IR sensor. Additionally, the inaccuracies may be impacted by different timing between frames and/or between lines.

Therefore, in accordance with aspects of the disclosure, the thermal sensor array 200 may be calibrated in advance using a preset target pattern having a known or fixed IR signature. From this calibration, corresponding offset currents can be determined that can be used to cancel the effects such as the DC component (e.g., normal current experienced at beginning of biasing an unheated IR sensor), bias heating, and the variance between pixels during the pulse biasing, and signal integration cycle.

The offset currents, received from the processor 110 may be subtracted (added) from the actual sensed currents during biasing of the thermal sensors by the current drivers 210, and the resulting difference currents may be amplified through a preamplifier (e.g., through corresponding current amplifiers) and integrated to produce the analog voltage signals corresponding to the IR flux sensed by the pixels.

The analog signals corresponding to the IR flux sensed by the pixels are converted by analog-to-digital converters (ADC) 215 of the ROIC 250 into digital image signals. In an aspect of the disclosure, the number of ADCs 215 is the same as the number of columns in the thermal sensor array 200.

The ROIC 250 may comprise output circuitry 220. The output circuitry 220 may include a multiplexor to combine the digital image signals for a row for output (to the processor 110).

The ROIC 250 may determine the timing for each processing event based on the received pixel clock and frame synchronization command(s) and line synchronization command(s). For example, different processes may occur in different pixel clock cycles. For example, generating the offset currents (from the offset current values received from the processor 110), biasing (and measuring) the IR sensors, offsetting (or normalizing) the measured currents with the offset currents, and integrating the normalized currents may occur in a pixel clock cycle, converting the integrated (analog) signals from the biased sensors to corresponding digital signals in the next pixel clock cycle, and outputting the digital signals in the next pixel clock cycle.

In an aspect of the disclosure, once the processor 110 receives the image data (digital signals) for all the rows in a frame, the processor 110 generates an image of the frame for display on a display 120. The processor 110 knows that the image data is for a last row of a frame based on the frame bit 325 received from the FPA 105.

In an aspect of the disclosure, the anti-detection mechanism 115 comprises a digital micromirror device (DMD). A DMD is an optical micro-electrical-mechanical system (MEMS) and is a spatial light modulator. The DMD 515 includes an array of micromirrors. The micromirrors may be aluminum and reflective. The array of micromirrors is arranged in a plurality of rows and columns. The individual micromirrors can be rotated into two states. Each micromirror corresponds to a DMD pixel. Each DMD pixel has a cell forms from a CMOS element. The micromirror is held by a torsional hinge. The DMD pixel also has two electrodes which are used to hold the micromirror in the two positions.

The number of rows and columns of micromirrors for the DMD 515 may be selected to correspond to the number of rows and columns in the thermal sensor array 200. For example, a DMD 515 may have 1024 columns and 768 rows to match the thermal sensor array 200 having the same number of rows and columns such that a DMD pixel corresponds to a pixel of the thermal sensor array 200. In other aspects of the disclosure, when the size of the DMD 515 is larger than the size of the thermal sensor array (greater number of rows and columns), the DMD 515 and thermal sensor array 200 may be oriented such that the thermal sensor array 200 is centered with respect to the DMD 515. When the DMD 515 and the thermal sensor array 200 are different sizes, there may not be a 1:1 correspondences to a mirror on the DMD and a pixel on the thermal sensory array 200. For example, when the DMD 515 have twice as many mirrors in each linear dimension as the thermal sensory array 200 (pixels), then there may be a 4:1 correspondence of mirrors to pixel. Additionally, when the thermal sensor array 200 has twice as many pixels per linear dimensional as mirrors in the DMD, the correspondence may be 1:4 mirrors to pixel.

The micromirrors of the DMD are arranged with a micromirror pitch. In accordance with aspects of the disclosure, selection of the DMD may be based on the expected wavelengths of the emitted by the target 500. For example, when the expected target 500 has a signature in the IR region, the micromirror pitch may be relative large. For example, a DMD 515 available from Texas Instruments may be used such as, but not limited to, DLP7000. This DMD has a pitch of 13.68 μm.

The DMD also as a window or cover. In an aspect of the disclosure, the window may be transmissive of a target wavelength range. For example, when the expected signature of the target is IR, the window may be ZnSe, or Ge.

Figure 6:
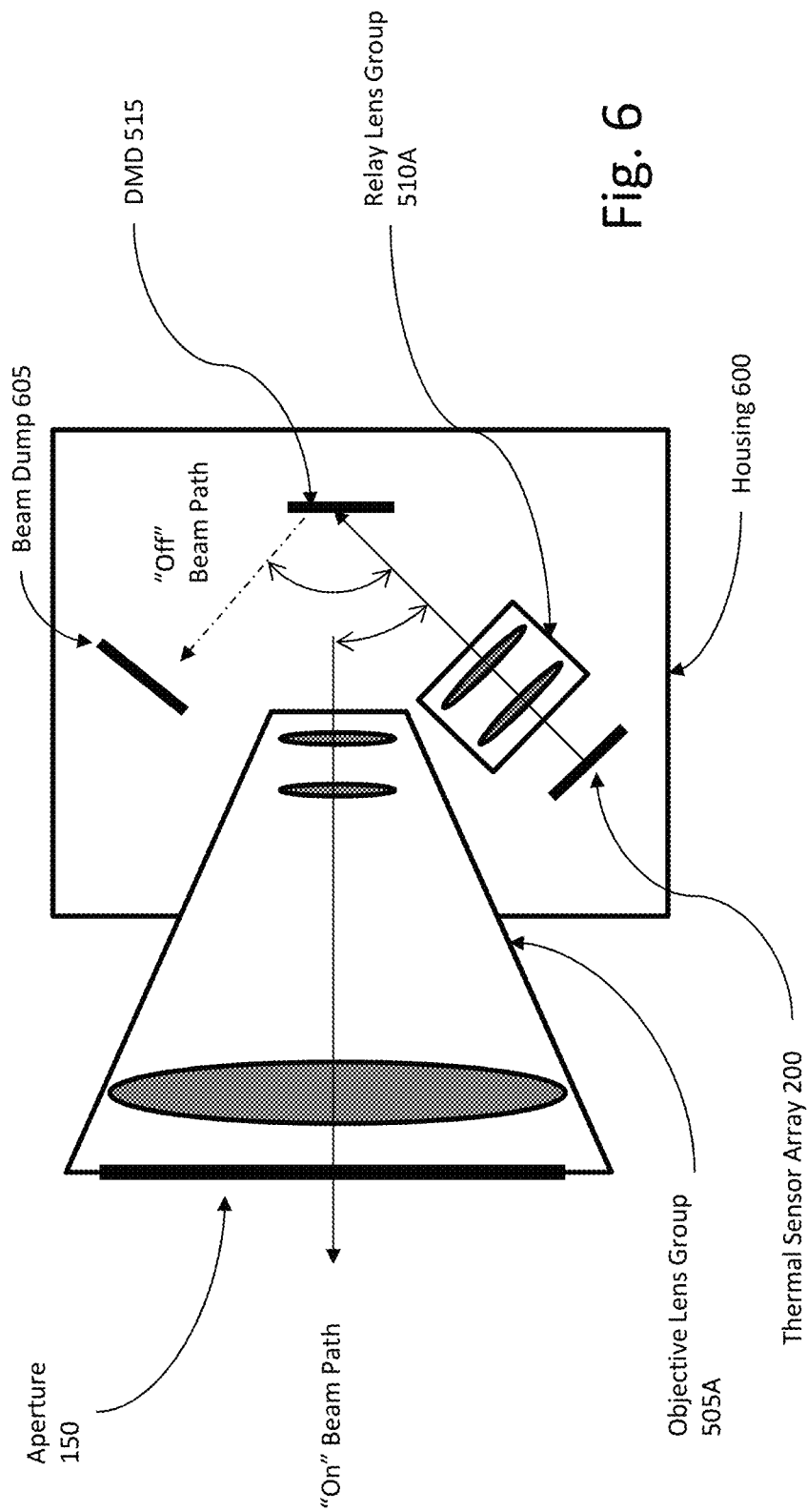
FIG. 6 depicts a sectional view of the system having the anti-detection mechanism of FIG. 5 in accordance with aspects of the disclosure.

FIG. 6 illustrates the DMD 515 mounted within the system 1. FIG. 6 is a sectional view. In an aspect of the disclosure, the DMD 515 is mounted via a frame (not shown) to the housing 600. The frame may be orthogonal to the mounting surface of the housing 600. In other aspects of the disclosure, the housing may have a projection and the DMD 515 is attached to the projection. The DMD 515 is positioned at an intermediary focal plane of the optics 125. When the DMD 515 is not powered, the micromirrors are orthogonal to the incident beam path. FIG. 6 also illustrates a beam dump 605. In an aspect of the disclosure, the beam dump 605 may be a projection from the housing 600. The projection may comprise a material which is absorptive to emissions of the thermal sensor array 200. In other aspects of the disclosure, the projection may be coated with a material that is absorptive. The coating may be an absorptive paint. In other aspects of the disclosure, the projection may comprise a material which is diffusely reflective. In other aspects of the disclosure, the projection may be scratched or otherwise textured to create a diffusely reflective surface. The position of the beam dump 605 may be based on the DMD 515 used and position of the DMD. The beam dump 605 may be physically displaced from the objective lens group 505A and the relay lens group 510A. The micromirrors of the DMD have two states, an "ON" state where the light is directed from the scene toward the thermal sensor array 200 and an "Off" state where light is directed from the thermal sensor array 200 toward the beam dump 605.

Figure 7:
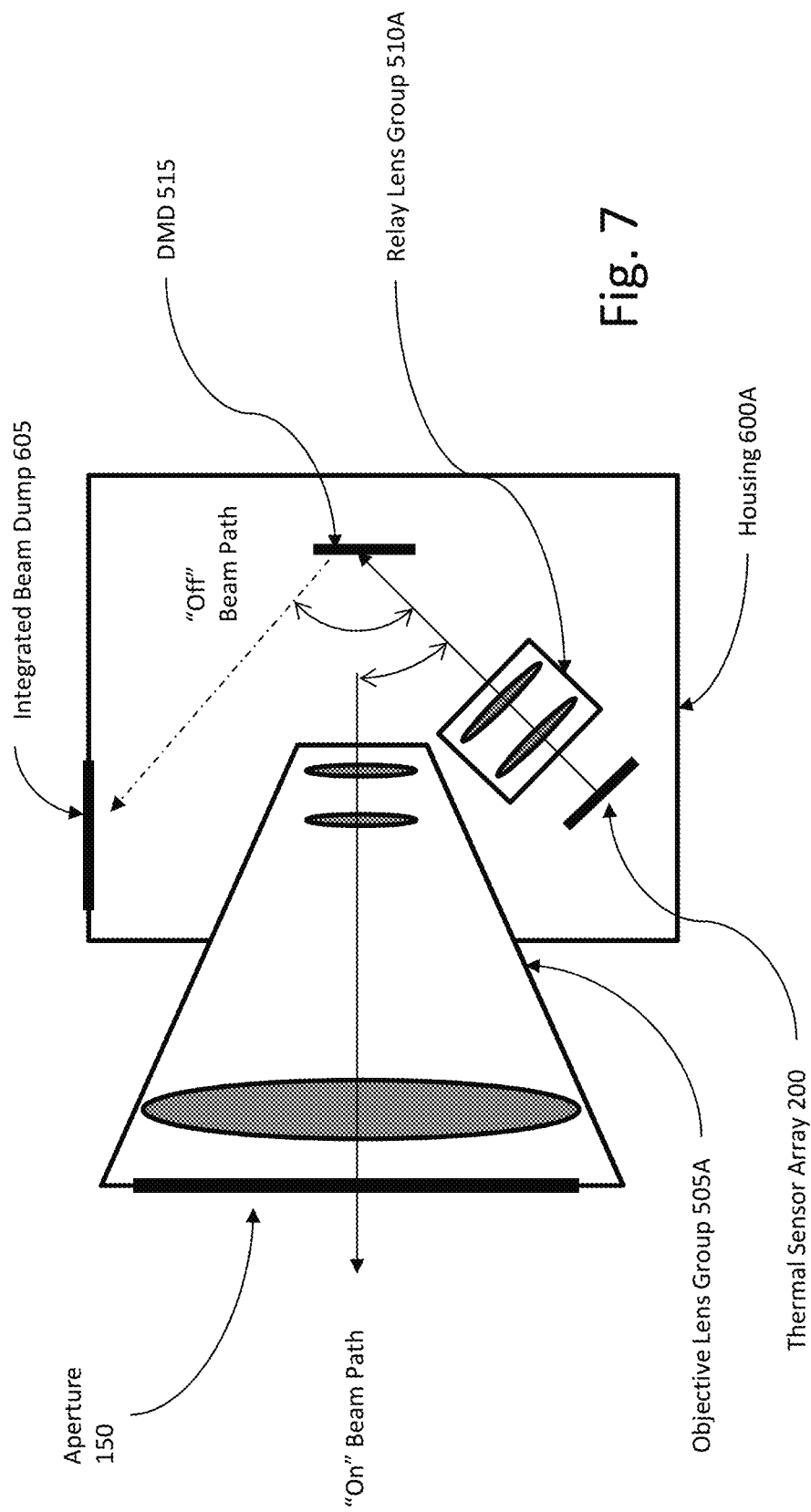
FIG. 7 depicts another sectional view of the system having the anti-detection mechanism of FIG. 5 in accordance with other aspects of the disclosure.

In other aspects of the disclosure, the beam dump 605 may be integrated into the housing 600A as shown in FIG. 7. The housing may have a portion comprised of a material which is absorptive to emissions of the thermal sensor array 200.

Different DMDs 515 may have different tilt angles. For example, the tilt angle may be +−12°. In an aspect of the disclosure, the angle between the objective lens group 505A and the relay lens group 510A may be twice the tilt angle in the on position. For example, when the tilt angle is 12°, the angle between the objective lens group 505A and the relay lens group 510A is 24°. The relay lens group 510A reimages the DMD focal plane onto the thermal sensor array 200. However, other tilt angles may be used.

When the micromirrors of the DMD are in the On position, light coming from a target 500, e.g., scene, is collected and focused by the objective lens group 505A, reflected by the DMD 515 and reimaged at the relay lens group 510A and directed to the thermal sensor array 200 during readout, emissions are reflected back toward the relay lens group 510A and reflected by the micromirrors of the DMD back through the objective lens group 505A (see "On' Beam Path in FIG. 6).

When the micromirrors of the DMD are in the Off position, emissions from the thermal sensor array 200 are directed toward the relay lens group 510A and reflected by the micromirrors of the DMD toward the beam dump 605. The beam dump 605 either absorbs the light (absorptive material) or diffusely reflects the light away from the objective path. Also, when the micromirrors of the DMD are in the Off position, light from the scene (detection target 500) may be directed toward a portion of the camera surface. The angle of the light may be based on the reflective angle of the micromirror and the objective axis. The direction is between the objective axis and the beam dump 605. In some aspects of the disclosure, the housing 600/600A may also include a second beam dump located in the path to control the stray light in the device.

When the DMD 515 is mounted within the system 1 there is a less than 1 pixel tolerance such that the 1 to 1 relationship between the DMD pixel and the thermal sensor array pixel can be achieved (when the DMD 515 and the thermal sensor array 200 are the same size). In an aspect of the disclosure, this relationship may be determined during a calibration phase. For example, in an aspect of the disclosure, a correspondence table 800 may be determined analytically from the position of the DMD 515 and magnification of relay lens group 510A and size ratio of the DMD 515 and the thermal sensory array 200. In another aspect of the disclosure, the correspondence table 800 may be determined by directing the system 1 toward a known target (signature) and selectively turning OFF/ON each mirror and observing the attached pixel of the thermal sensor array 200 and recording the same in the correspondence table 800. FIG. 8 illustrates an example of a correspondence table. In one example, the correspondence table 800 may be set up by rows (as shown). In other aspects of the disclosure, the correspondence table may include each pixel of the DMD and thermal sensor array. This correspondence table 800 is used by the processor 110 to select the corresponding micromirrors to be controlled. As noted above, there may be a 4:1 micromirror to pixel relationship. Therefore, the correspondence table 800 may have more than one micromirror associated with a single pixel such that more than one mirror is controlled as a single block. Also as noted above, there may be a 1:4 micromirror to pixel relationship. Therefore, the correspondence table 800 may be more than one pixel associated with a single mirror.

The DMD 515 may be controlled with a DMD controller 520. The DMD controller 520 is a digital controller. The DMD controller 520 may be used to control one type of DMD (family) or multiple different types of DMDs (families). When the DMD controller 520 controls one type of DMD 515, the DMD controller 520 may have prestored all of the bit control information and addresses (map of the rows of the DMD) to control the DMD. When the DMD controller 520 is capable of controlling multiple types of DMDs 515, a configuration chip, such as a DMD PROM may be used to provide a configuration bit stream which configures the controller to control a specify type of DMD. For example, a DMD controller available from Texas Instruments may be used such as DLPC410 for the DLP700 DMD. The PROM may be a DLPR410 PROM also available from Texas Instruments.

The DMD controller 520 receives control information from the processor 110, e.g., row or pixel information. The DMD controller 520 determines the addresses from the rows/pixels for loading and loads the row/pixel data into the memory of the DMD. The position/state of the micromirrors is changed when "reset" or a "clocking pulse" is received by a DMD micromirror driver. Thus changed on the angular position of the micromirror array first includes updates the contents of the memory (CMOS memory), e.g., loading and applying the clocking pulse or reset.

In some aspect of the disclosure, the DMD micromirror driver is integrated into the DMD 515. In other aspects of the disclosure, the DMD micromirror driver is external to the DMD 515. For example, a DMD micromirror driver available from Texas Instruments may be used such as the DLPA200. The driver may be an ASIC which supplies the voltage (necessary power) and clocking pulse to the DMD. The clocking pulse is supplied to the DMD 515 under the control of the DMD controller 520. The DMD controller 520 is supplied with the main clock generated by the processor 110 from the oscillator 100. In other aspects, the DMD controller 520 may be directly connected to the oscillator.

Figure 9A:
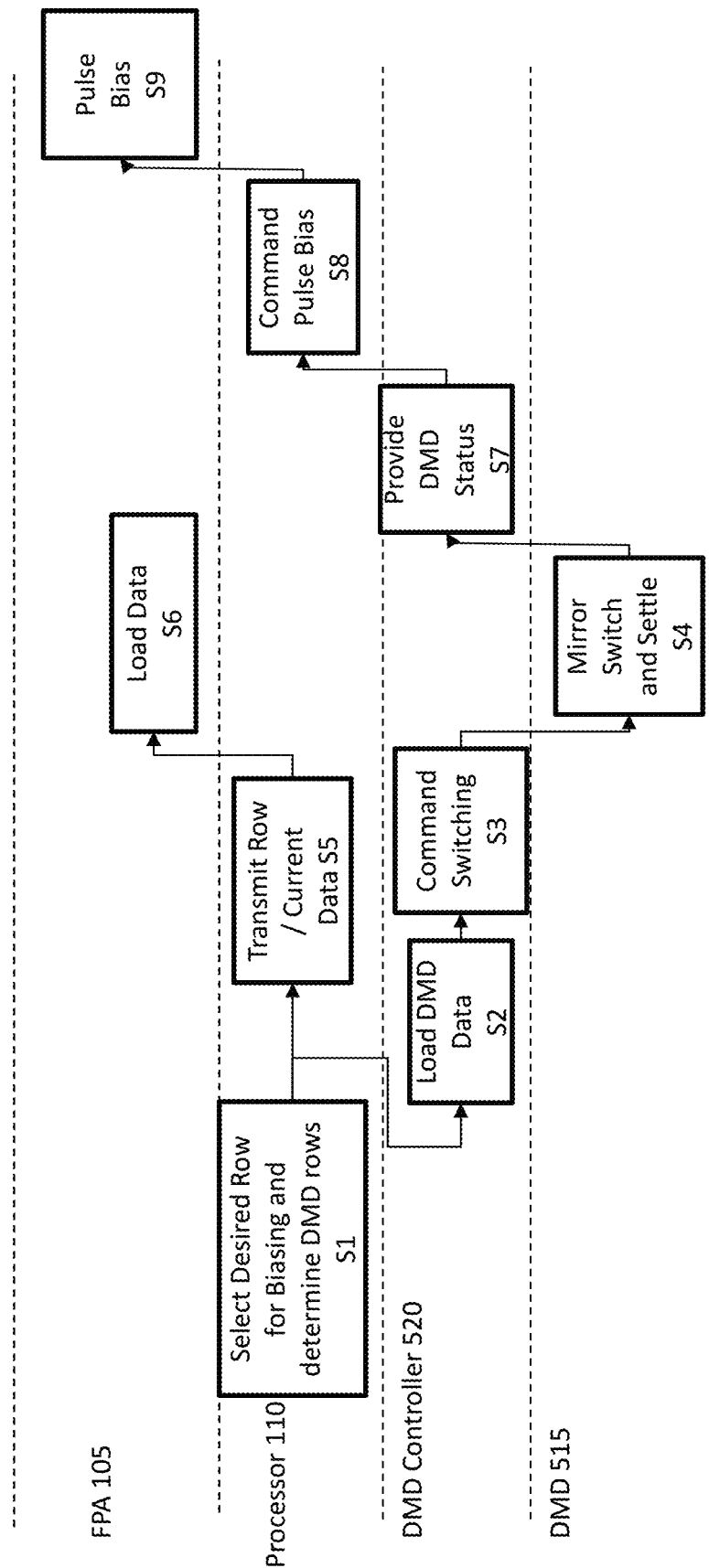
FIG. 9A depicts a flow for an anti-detection method in accordance with aspects of the disclosure.

In accordance with aspects of the disclosure, the DMD 515 acts as a shutter and selectively rotates in conjunction with the readout of the frames. FIG. 9A illustrates a flow of controlling the DMD 515 in conjunction with reading out a frame from the FPA 105. FIG. 9A also illustrates the interaction between the FPA (and ROIC 250), the processor 110, the DMD controller 520 and the DMD 515. In an aspect of the disclosure, the processor 110 manages the readout and the DMD 515 via the DMD controller 520. At S1, the processor 110 determines the row from the thermal sensor array 200 for bias. If it is the first row, the row may be the top or bottom row of the array 200. If not, the row may be the next row adjacent to a row being biased. The processor 110, using the correspondence table 800, determines the corresponding DMD row for the determined row of the array 200 (or pixels for the determined pixels). The processor 110 transfers the corresponding DMD row (or pixels) to the DMD controller 520. In an aspect of the disclosure, the processor 110 may also transmit the pulse timing or pulse clock to the DMD controller 520 for synchronization purposes. The DMD controller 520 receives the DMD row information and looks up the correspondence address for the row.

The DMD controller 520 loads the DMD data, e.g., the row(s) which is going to change angles, to the DMD 515, e.g., CMOS memory, at S2. The loading of the DMD data may take several clock cycles. After the data is loaded into the CMOS memory of the DMD, the DMD controller 520 instructs the DMD driver (not shown) to generate the clocking pulse or reset at S3. In response to receipt of the instruction, the DMD driver generates the clocking pulse to the specified pixels (row) and provides the necessary voltage. At S4, the micromirrors of the DMD switch states, e.g., from ON to OFF (to direct light toward the beam dump). The micromirrors take time to move and settle. The amount of time may vary depending on which DMD 525 is used.

In an aspect of the disclosure, in parallel with S2-S4, the processor 110 transmits the current offset data and row information to the FPA 105 (ROIC 250) via the bit line 310. The current offset is loaded into the ROIC for the specific row at S6.

Once the micromirrors have switched and settled, the DMD 515 may report the change to the DMD controller 520 via a reset signal or another signal. In response to the reception of the signal, the DMD controller 520 transmits the status to the processor 110 at S7.

The processor 110 receives the status and in response, generates a pulse bias command for the row at S8. The pulse bias command is transmitted to the FPA 105 (ROIC 250) via the command line 300.

At S9, the ROIC 250 pulse biases the row, the currents are measured, adjusted with the bias, and the image data is transferred to the processor 110. An image of the scenes is still able to be generated, even though, while the row is being pulse bias, the light is reflected to the beam dump 605 due to the thermal relaxing time of the sensing element. Once, the image data for the row is received by the processor 110, the processor selects the next desired row at S1.

Since S5-S6 are done in parallel with S2, S3, S4 and S7, the rate frame is not impacted by the use of the DMD 525. For example, a frame rate of 60 Hz for an 1024 columns and 768 rows array, has a pulse bias command on the order of every 20 μs-25 μs. The time to load, switch and report the status of the angular rotation is less than 20 μs-25 μs.

In an aspect of the disclosure, more than one row of the DMD 515 may be rotated to the off state. This is due to the thermal relaxing time of the sensor elements. For example, while a second row is being pulse biases, the DMD row corresponding to the first thermal sensor row may still be OFF. The number of rows maintained in the OFF state may be being on the thermal relaxing time of the sensor elements of the thermal sensor array 200. If the DMD row were to return to an ON state when the sensor element were still excited, e.g., not relaxed, emission from the array 200 may be emitted outside of the system 1. The DMD 525 and FPA data transfer is significantly faster than the pixel thermal relaxation time, the DMD will continue blocking for more than one row depending on the ratio of the thermal relaxation time of the pixel.

Thermal relaxation is an exponential decay (i.e. a first-order continuous process) and is parameterized by a single time constant. Blocking (interruption) time for each pixel is determined based on the amount of signature reduction required (e.g. 50%). To maintain synchronization, the blocking time is an integer multiple of the FPA line read time.

Figure 9B:
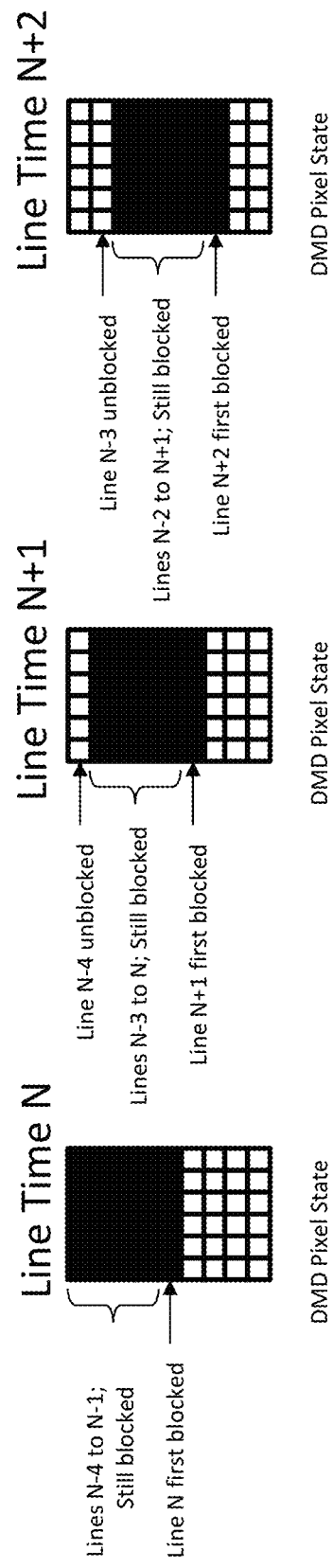
FIG. 9B depicts a timing diagram for the control of the DMD and pulse biasing in accordance with aspects of the disclosure.

FIG. 9B shows an example of multiple rows (lines) of the DMD being OFF at three different times, N, N+1 and N+2. In the example 5 rows are OFF. However, the disclosure is not limited to a block of 5 rows (lines). A block of 5 is shown just for descriptive purposes only. As shown in Line time N, line N is newly turned OFF (blocked, direct light to toward the beam dump 605). Lines N−1 to N−4 are still Off (blocked). At Line time N+1, the shutter moves and the N+1 line is newly turned OFF, however, now, N−4 is turned ON (direct light toward the thermal sensor array 200) and N to N−3 lines are still OFF (blocked). At Line time N+2, line N+2 is newly turned OFF (blocked). Now both N−3 is turned ON. N+1 to N−2 is still OFF.

Thus, in accordance with the above aspects, emissions from the thermal sensor array 200 are directed to a beam dump 605 instead of being emitted outside the system 1 during readout of the row and during its relaxation time. Thus, the DMD acts as a shutter.

Figure 10:
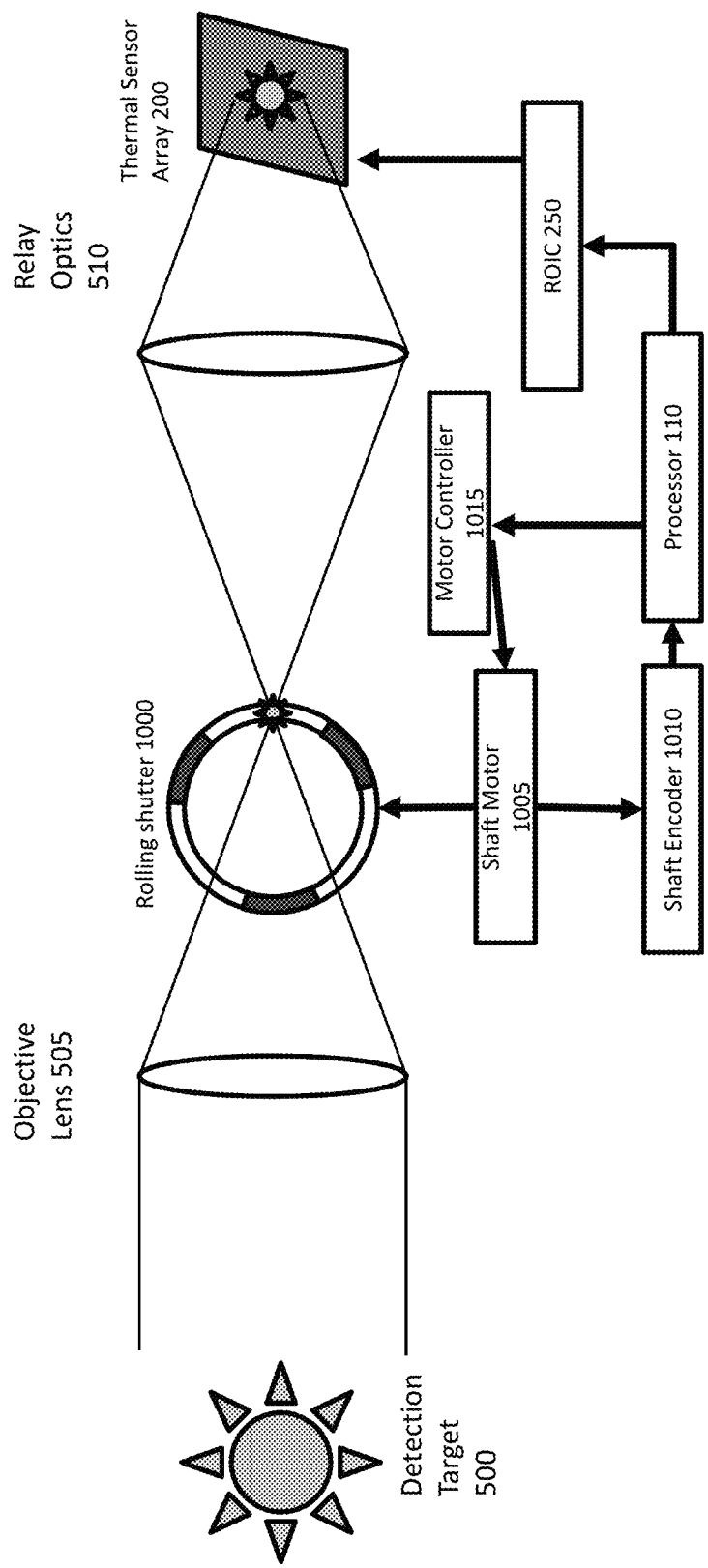
FIG. 10 depicts anti-detection mechanism in the system in accordance with aspects of the disclosure using a rolling shutter.
Figure 16:
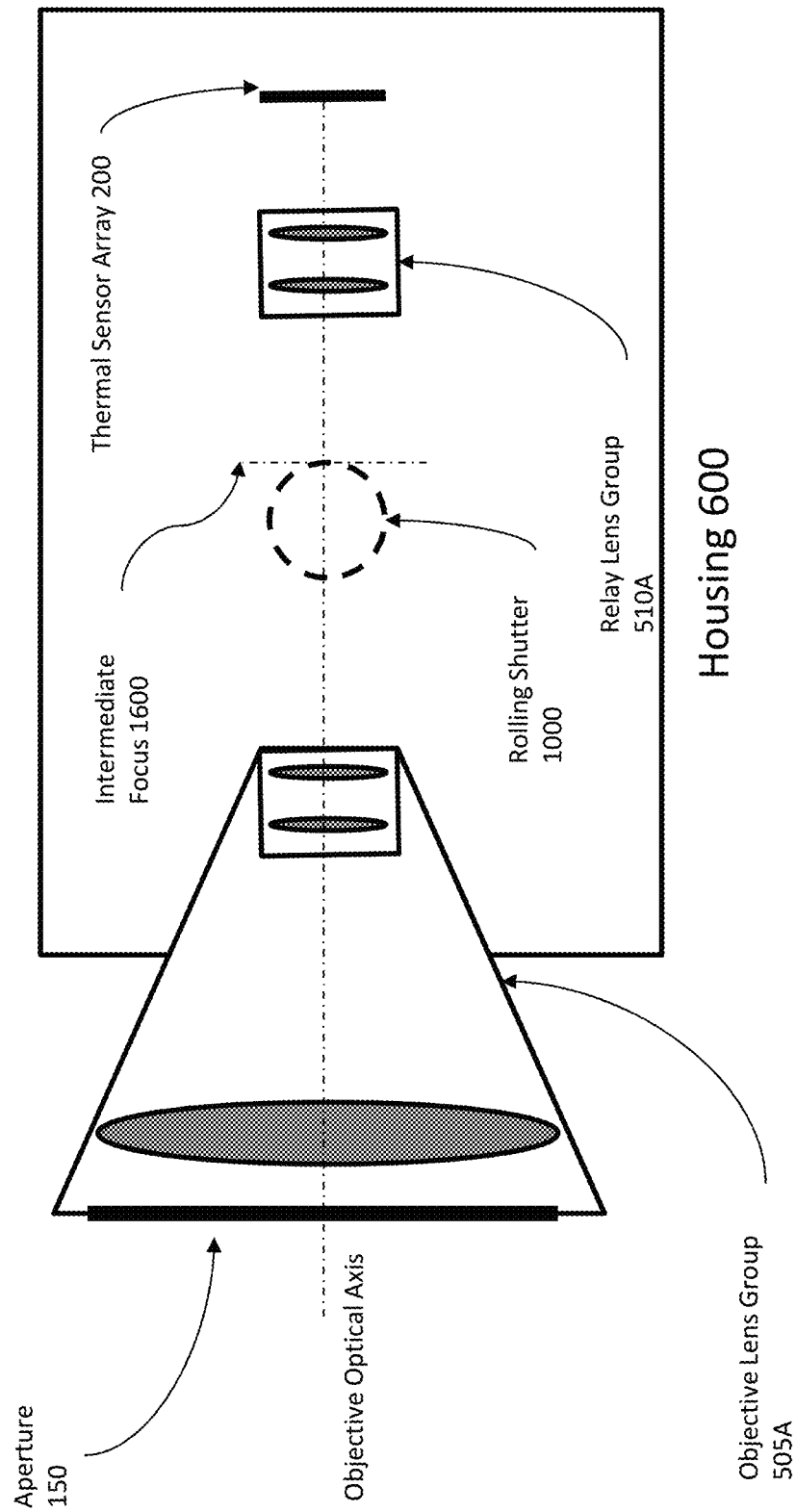
FIG. 16 depicts a sectional view of the system having the anti-detection mechanism of FIG. 10 in accordance with aspects of the disclosure.

In another aspect of the disclosure, the anti-detection mechanism 130 may comprise a rolling shutter 1000 instead of the DMD 515. FIG. 10 illustrates a diagram of a rolling shutter 1000. FIG. 16 shows the rolling shutter in a housing 600. The rolling shutter 1000 may be cylindrical. In an aspect of the disclosure, the rolling shutter 1000 may have a plurality of opaque sections and a plurality of transmissive sections (shown in FIG. 11 as shutter sections 1120). The opaque sections may not transmit light at the expected wavelength signature of the target 500. The opaque sections may be treated with paints or other materials, e.g., metallization. In other aspects of the disclosure, the opaque sections may be sparse metallic wires. The gauge of the wire may be determined by the longitudinal length of the shutter 1000 and number of sections such that the wires are structural and avoid vibrations as the shutter 1000 rotates. In some aspects, more than one shaft motor may be used for symmetric rotation of the shutter 1000.

In an aspect of the disclosure, at least a portion of the shutter is located at an intermediary focal plane (intermediary focus 1600) of the relay optics 510. While one portion of the shutter is at the intermediary focal plane (intermediary focus 1600), the opposite side of the shutter may pass through the path of the light. However, given the size of the opaque sections and the location of the opposite side (out of the image plane), the impacts on the image are small. As shown in FIG. 16, the objective lens group 505A, the rolling shutter 1000, the relay lens group 510A and the thermal sensor array may be aligned and centered with respect to the optical axis. The size of the opaque sections may be based on the size of the pixels of the thermal sensor array, number of rows, thermal relax time for each element, and ratio of the intermediate focal size and the final focal size. For example, the larger the opaque section is, the more rows can be blocked at the same time. Thus, the size of the opaque sections may be larger if there is a larger thermal relax time of the elements. Relay optics 510 (or relay optics group) have an associated magnification (magnification factor) that relates to the image planes at the intermediate focus 1600 and the final focus (at the thermal sensor array 200). For a magnification factor of M (i.e. shutter plane is M-times bigger than the final focus) and a pixel dimension of P, a line read rate of R, and a relaxation time of T: the opaque section may be determined as follows: M*P*(1+R*T). In some aspects of the disclosure, the opaque section(s) may be made to be larger than the detected sized based on the above to accommodate unknown or uncontrollable elements, e.g., safety factor.

The size of the transparent or transmissive sections may be determined by the target duty cycle. The transparent and opaque sections may alternate.

Figure 11:
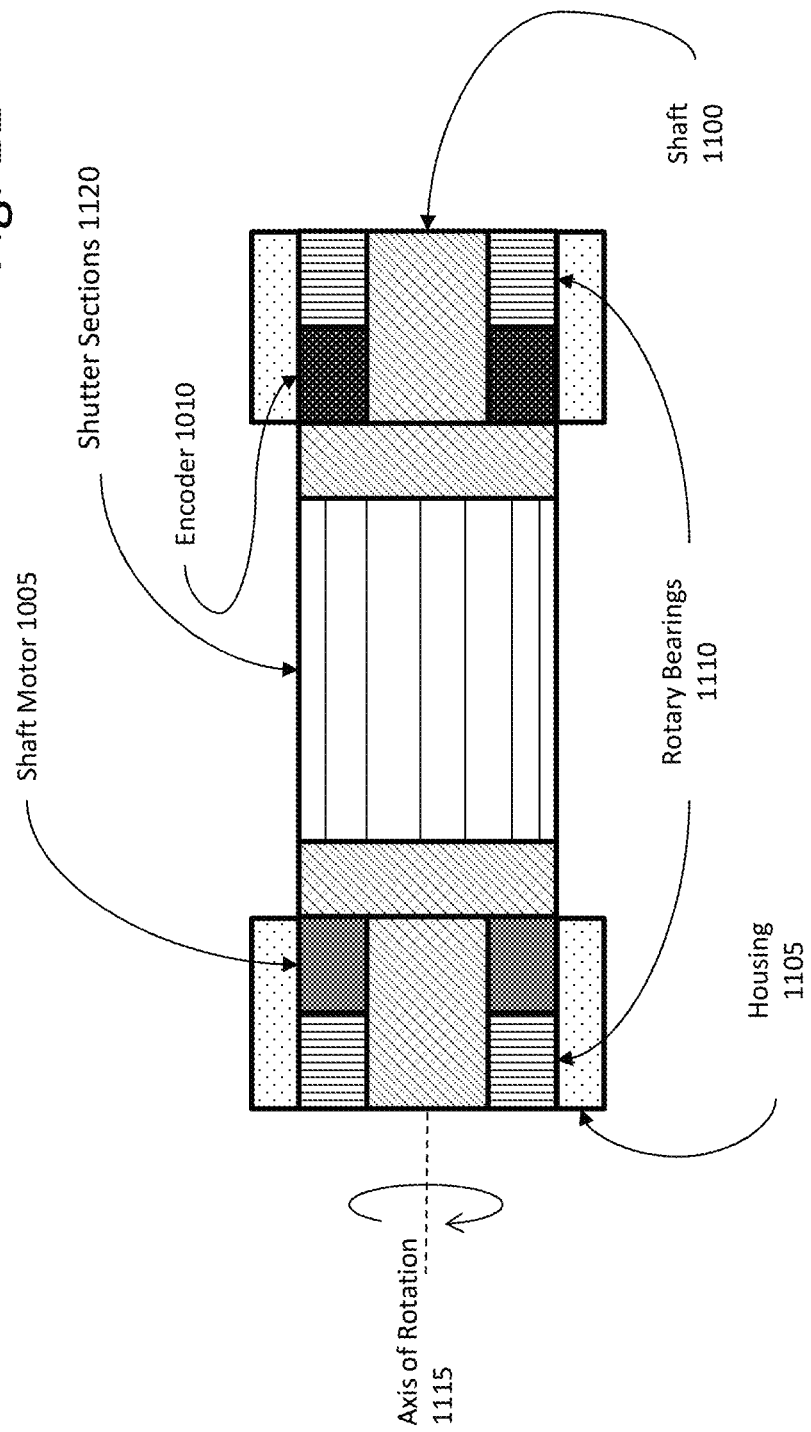
FIG. 11 depicts a sectional view of portions the anti-detection in accordance with aspects of the disclosure.

The shutter 1000 may be attached to a shaft as shown in FIG. 11. The shaft 1100 may be a split axial shaft. FIG. 11 is a sectional view of the shutter assembly. The shaft 1100 is attached to a shaft motor 1005. The shaft motor 1005 controls the position and/or speed of the shaft 1100 which in turn determines the position and speed of the shutter 1000. The shaft 1100 is also connected to an encoder 1010. The encoder 1010 may be a rotary encoder configured to detect the position of the shaft. In other aspects of the disclosure, a RPM speed sensor may be used to determine the speed of the shaft 1100.

The axial shaft 1100 has an axis of rotation 1115. The shaft 1100 rotates with respect to a frame. In some aspects, the frame of the assembly is a housing 1105. A portion of the housing 1105 may be the same as the housing of the system. In other aspects, the housing 1105 may be attached to the system housing. The rotary bearings 1110 enable the shaft 1100 to rotated with respect to the housing 1105.

In an aspect of the disclosure, the shaft motor 1005 may be an AC motor. The motor controller 1015 may be an AC motor controller. The AC motor controller may produce one or more commands to the shaft motor 1005 causing the motor to change speed and/or position. In an aspect of the disclosure, the motor control may be implemented using a closed loop control. For example, the shaft encoder 1010 or RPM sensor may sense the velocity (speed) of the shaft 1100 and compute a velocity error and modulates the electrical power to generate a motor power signal in accordance with the motor type and control, to the shaft motor 1005. In other aspects, instead of velocity (speed), the position is sensed by the shaft encoder 1010 and a position error is computed by the AC motor controller. The AC motor controller modulates the electrical power to generate a motor power signal in accordance with the motor type and control, to the shaft motor 1005.

In other aspects, the shaft motor 1005 may be a brush or brushless DC motor. The motor controller 1015 may be a DC motor controller.

The modulation of the motor power signal may vary based on the motor type and may be a pulse-width modulation (PWM), a variable DC level, variable amplitudes one or more AC signals or parallel pulses. The motor controller 1015 is supplied with electrical power (not shown) needed to supply the modulated motor power signal.

The motor 1005 may be directed connected to the shaft 1100. In other aspects, the motor 1005 may be connected via gears, belts, chains, etc. . . . . .

The motor controller 1015 may be in communication with the processor 110. The communication may be via analog or digital signals. The processor 110 controls the movement of the shaft 1100 (and thus the transparent and opaque sections)

(via the motor controller 1015) and the timing of the pulse bias commands for the row(s). In accordance with aspects of the disclosure, the shaft 1100 is controlled such that emissions are blocked when the row is read by the ROIC 250 and during the thermal relax time.

Figure 12:
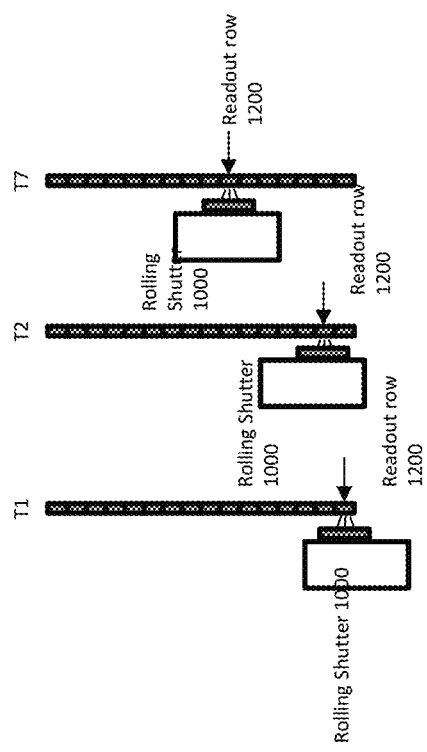
FIG. 12 depicts the rolling shutter blocking the rows while readout is occurring in accordance with aspects of the disclosure.

FIG. 12 illustrates an example of the position with respect to the readout row 1200 for times: T1, T2 and T7 (three different times). As illustrated, the rolling shutter 1000 blocks the respective row. For example, when the first row is readout, the rolling shutter 1000 blocks the first row, when the second row is being readout, the roller shutter 1000 blocks the second row and when the seventh row is being readout, the rolling shutter 1000 blocks the seventh row. In an aspect of the disclosure, the opaque section is designed to block more than one row because of the thermal relax timing. For example, when the second row is being readout, both the first and second rows may be blocked.

As described above, there may be two modes of controlling the shaft: a position mode and a speed mode. In position mode, the motor controller 1015 command a position based on an instruction from the processor 110. The relationship between the shaft position (opaque sections) and the rows of the thermal sensor array 200 may be determined in advance in a calibration phase. In an aspect of the disclosure, the relationship may be determined by repeatedly rotating the shaft to different rotations, e.g., angles, maintaining the shaft at the position for a period of time and observing the image of a known target after the period of time and comparing the measured image to a completely unblocked image and measuring the location of the occlusion. The period of time may be based on the thermal relaxation period of the thermal sensor array 200. The determined relationships may be populated into a correspondence table 1300. The correspondence table 1300 includes each shaft position and its associated row of pixels. An example of a correspondence table is shown in FIG. 13. The calibration also determines the valid step sizes between positions of the shaft, e.g., the angular rotation needed to move from one row to another row. The shaft position corresponds to where the opaque section is in line of sight of the row.

Figure 14:
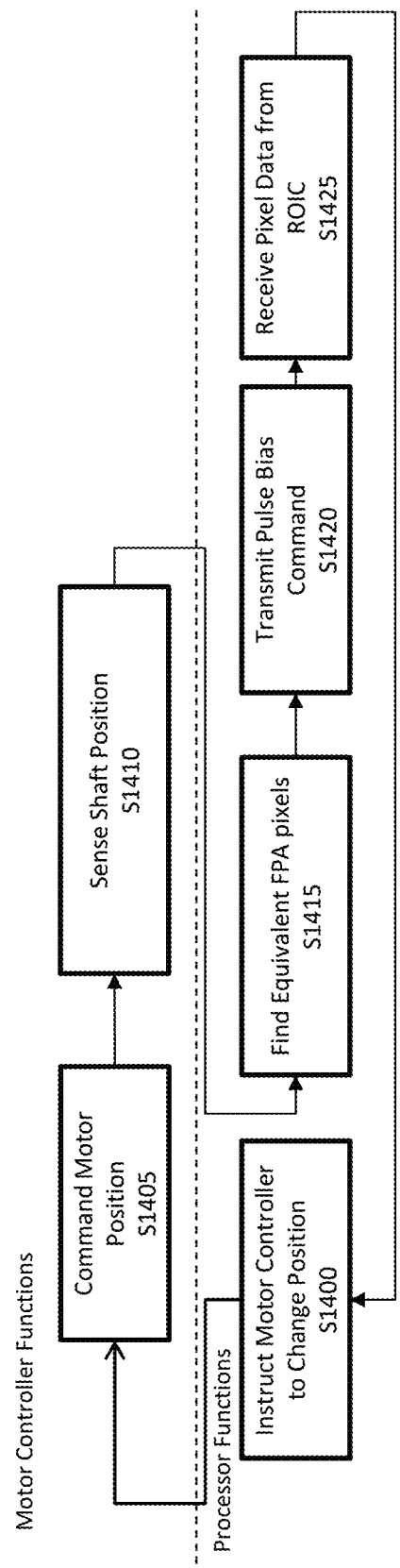
FIG. 14 depicts a flow for an anti-detection method in accordance with aspects of the disclosure using position mode.

FIG. 14 illustrates a functional diagram showing readout/motor control in position mode in accordance with aspects of the disclosure. The processor 110 functions are shown on the bottom and the motor controller 1015 functions are shown on the top. At S1400, the processor 110 instructs the motor controller 1015 to change the position of the shaft 1100 to a next valid position, e.g., to the next row. In response, at S1405 the motor controller 1015 determines the error, e.g., the difference between the current position and the instructed position and modulates the power to the shaft motor 1005 to change the position. In an aspect of the disclosure, the initial difference is known based on the valid step size, e.g., rotation between adjacent rows. The shaft position is continuously sensed by the shaft encoder 1010 and feedback to both the motor controller 1015 and the processor 110. The motor controller 1015 uses the feedback position to confirm that the shaft 1110 has reached the instructed position and to modulate the power based thereon at S1410. The processor 110 uses the determined position to determine when to transmit a pulse bias command to the ROIC 250. The processor 110 determines when the shaft 1100 is located at a row, e.g., next valid position. When the processor 110 determines that the shaft 1100 is located at a row, the processor determines the row of the thermal sensor array 200 using the correspondence table 1200. The processor 110 uses the position of the shaft 1100 to find the corresponding row of pixels at S1415. Once the corresponding row of pixels is identified, the processor 110 issues a pulse bias command via the command line 300 to the ROIC 250 at S1420. The ROIC 250 biases the row and the current is measured and the offsets are applied (for that row or pixels). The ROIC 250 generates the data for the row and sends the data to the processor 110, e.g., pixel data at S1425. Once the pixel data for the row is received, the processor 110 instructs the motor controller to move the shaft to the next row, e.g., next valid position, at S1400.

S1400-S1425 is repeated for each row of the frame. Once the frame is finished, e.g., last row, S1400-S1425 is repeated for the next frame. The rotation of the shutter 1000 is in the same direction as the readout direction.

Figure 15:
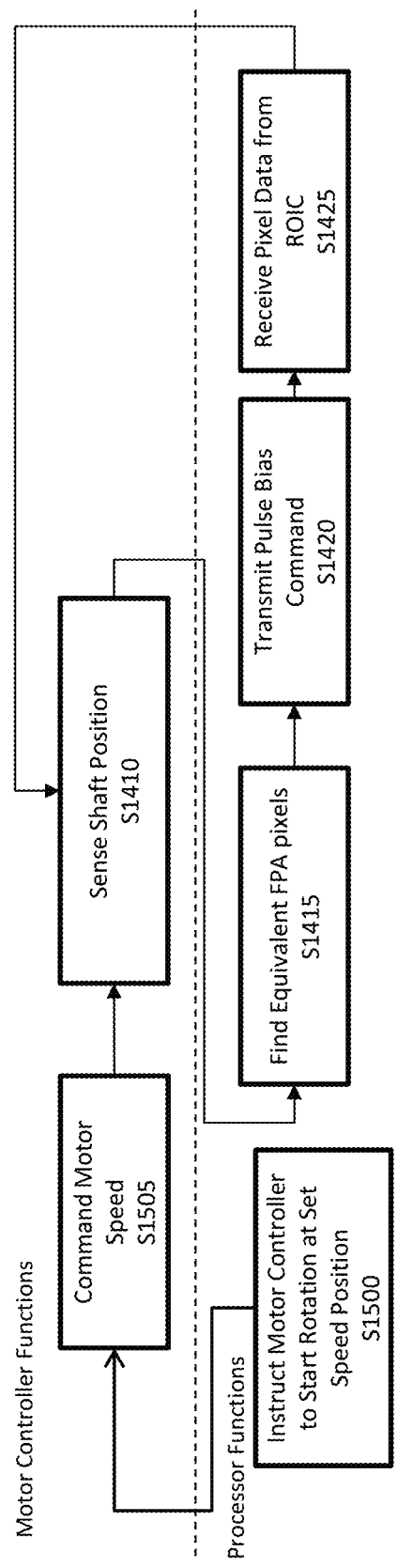
FIG. 15 depicts a flow for another anti-detection method in accordance with aspects of the disclosure using speed mode.

FIG. 15 illustrates a functional diagram showing readout/motor control in speed mode in accordance with aspects of the disclosure. The processor 110 functions are shown on the bottom and the motor controller 1015 functions are shown on the top. In speed mode, the motor 1005 is commanded to a preset constant velocity. The preset constant velocity is determined by a desire frame rate and the number of alternative transparent/opaque sections. At S1500, the processor 110 instructs the motor controller 1015 to start moving the shaft 1100. The instruction may include the preset constant velocity. In response, at S1505, the motor controller 1015 determines the error, e.g., the difference between the current speed (e.g., zero) and the instructed speed and modulates the power to the shaft motor 1005 to change the speed. The position of the shaft is continuously sensed by the shaft encoder 1010. In an aspect of the disclosure, the speed may also be sensed by an RPM sensor. The motor controller 1015 uses the feedback position (speed) to confirm that the shaft 1110 has reached the instructed speed and to modulate the power based thereon at S1410. The processor 110 uses the determined position to determine when to transmit a pulse bias command to the ROIC 250. The processor 110 determines when the shaft 1100 is located at a row, e.g., next valid position. When the processor 110 determines that the shaft 1100 is located at a row, the processor 110 determines the row of the thermal sensor array 200 using the correspondence table 1200. The processor 110 uses the position of the shaft 1100 to find the corresponding row of pixels at S1415. Once the corresponding row of pixels is identified, the processor 110 issues a pulse bias command via the command line 300 to the ROIC 250 at S1420. The ROIC 250 biases the row and the current is measured and the offsets are applied (for that row or pixels). The ROIC 250 generates the data for the row and sends the data to the processor 110, e.g., pixel data at S1425. Once the pixel data for the row is received, the processor 110 determines whether the shaft 1100 is located at the next valid position (and repeats S1415-S1425 for the remaining rows in the frame). S1505 and S1410-1425 is repeated for each frame.

In other aspects, instead of temporarily blocking a row while readout is occurring, mitigation may be achieved by moving either a relay mirror or the thermal sensor array 200 between frames. The movement may be random or based on a preset pattern. This movement effective spreads any emitted signature in the frequency domain, which limits the available signal processing gain for another imaging system.

For example, a known method for systems, which are used for thermal detection, to improve SNR for narrow frequency signals is correlating a series of measurements and computing the Fourier transform of the series. The noise in the series is proportional to the square-root of the number of samples and the signal energy is linearly proportional to the number of samples. Thus, the SNR scales as the square root of the number of sample points.

Additionally, the frequency resolution of the Fourier transform is inversely proportional to the sample time; e.g. a 0.1 second series has Fourier resolution of 10 Hz, a 1.0 second series has resolution of 1 Hz, a 10 second series has resolution of 0.1 Hz, etc. Detection of signal energy is simplest (i.e. SNR is maximized) when the energy is concentrated in a single frequency element of the Fourier transform. Occupying a single frequency element requires a signal bandwidth of less than the resolution of Fourier transform. Signals with bandwidth wider than a single element spread the signal energy across multiple elements. Detection is hardest (i.e. SNR is minimized) when the signal is spread across the maximum number of frequency elements. Aspects of the disclosure exploit this by spreading the signature over frequency such that the energy is not concentrated in a single frequency element.

Figure 17:
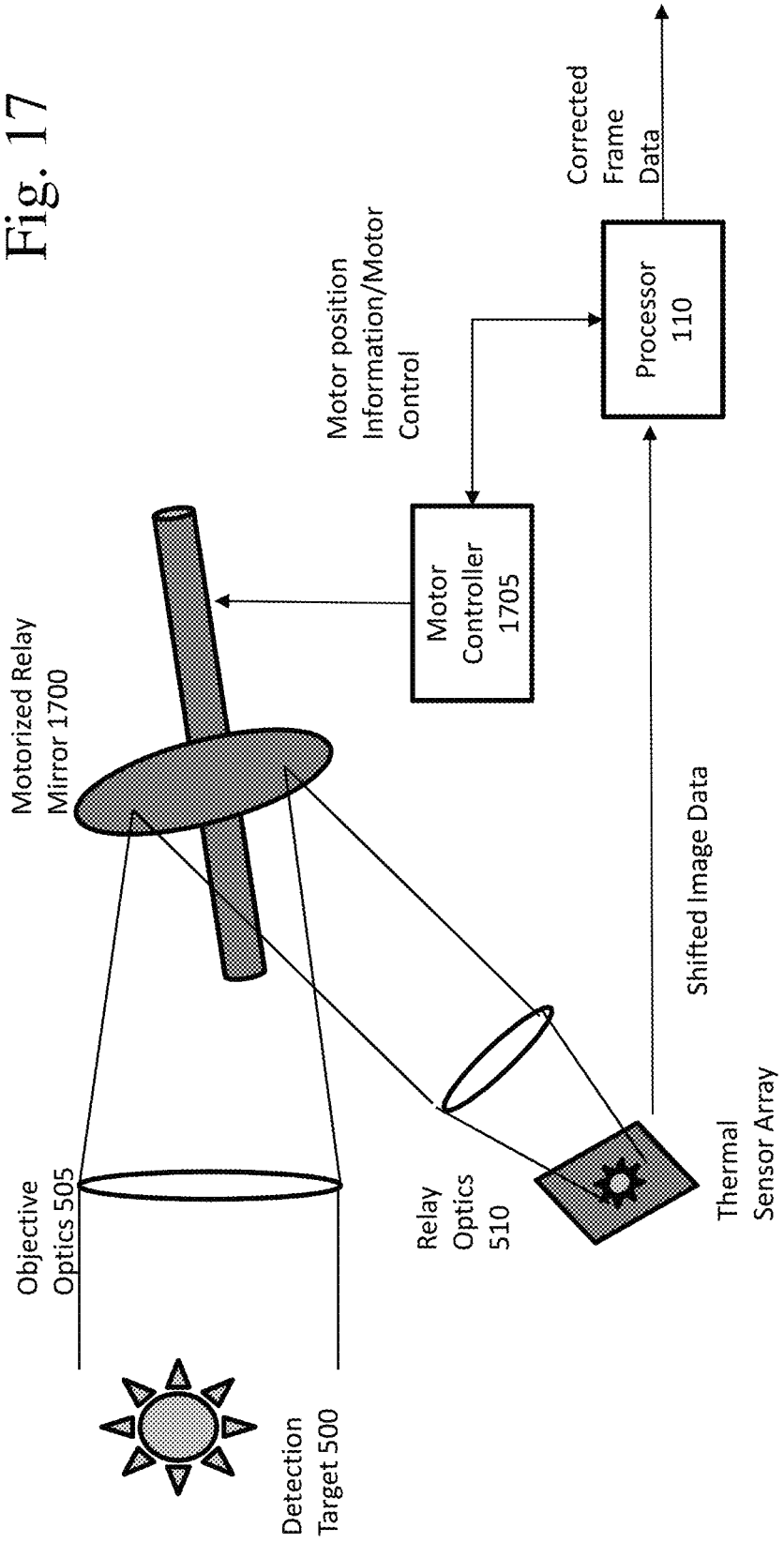
FIG. 17 depicts anti-detection mechanism in the system in accordance with aspects of the disclosure using motorized relay mirror.

FIG. 17 illustrates a diagram showing components of an anti-detection mechanism including a motorized relay mirror 1700 in accordance with aspects of the disclosure. The motorized relay mirror 1700 may be located at any position along the optical path between the optics 505, 510. However, in other aspects, the motorized relay mirror 1700 may be located at a pupil focal point. The mirror face (mirror) (shown in FIG. 18) may rotate with respect to a rotation axis. This rotation causes the image on the thermal sensor array 200 to be linearly translated. The angle of rotation is controlled by a motor controller 1705 and processor 110.

Figure 18:
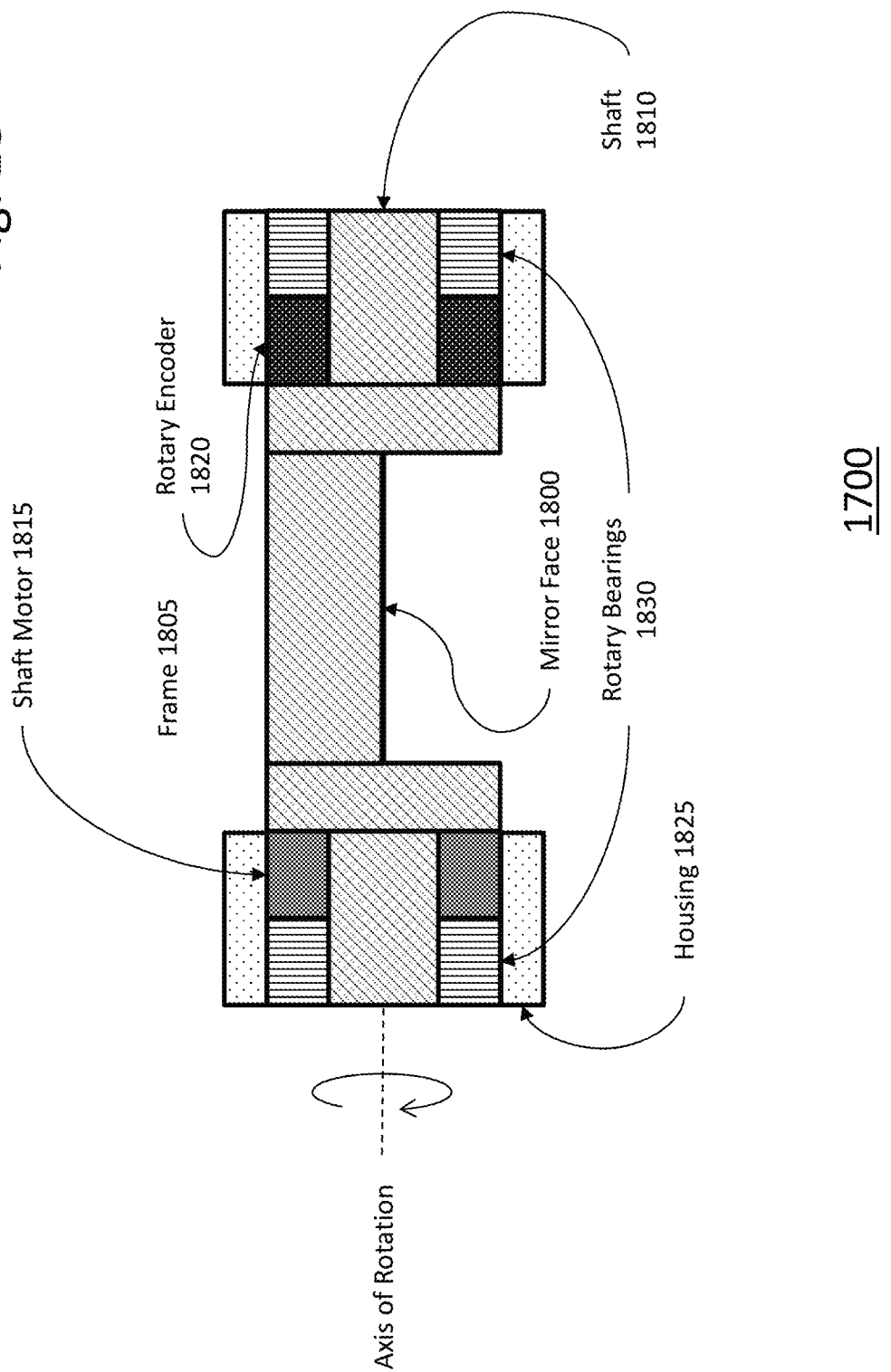
FIG. 18 depicts a sectional view of portions the anti-detection in accordance with aspects of the disclosure.

FIG. 18 is a sectional view of the motorized relay mirror 1700. The mirror face 1800 may be attached to frame or backing 1805. The frame 1805 may be attached to a shaft 1810. As shown in FIG. 18. The shaft 1810 may be a split axial shaft. The shaft 1810 is attached to a shaft motor 1815. The shaft motor 1815 controls the angle of the mirror 1800 with respect to the thermal sensor array. The shaft 1815 is also connected to an encoder 1820. The encoder 1820 may be a rotary encoder configured to detect the position of the shaft. In other aspects of the disclosure, a RPM speed sensor may be used to determine the speed of the shaft 1810.

The shaft 1810 has an axis of rotation 1840. As depicted in FIG. 18, the mirror face 1800 rotates into and out of the page. In some aspects, the frame 1805 is a projection of the housing 500. In other aspects, the housing 1105 may be attached to the housing 500. The rotary bearings 1830 enable the shaft 1810 to rotate.

In an aspect of the disclosure, the shaft motor 1815 may be similar to the motor described above. For example, the shaft motor may be an AC motor. The motor controller 1705 may be an AC motor controller. The AC motor controller may produce one or more commands to the shaft motor 1815 causing the motor to rotate the shaft 1810 which is turn rotates the mirror face 1800. In an aspect of the disclosure, the motor control may be implemented using a closed loop control. For example, the shaft encoder 1820 or RPM sensor may sense the position and thus the angle and compute an error and modulates the electrical power to generate a motor power signal in accordance with the motor type and control, to the shaft motor 1815. In other aspects, the shaft motor 1815 may be a brush or brushless DC motor. The motor controller 1705 may be a DC motor controller.

The modulation of the motor power signal may vary based on the motor type and may be a pulse-width modulation (PWM), a variable DC level, variable amplitudes one or more AC signals or parallel pulses. The motor controller 1705 is supplied with electrical power (not shown) needed to supply the modulated motor power signal.

The motor 1815 may be directed connected to the shaft 1810. In other aspects, the motor 1815 may be connected via gears, belts, chains, etc. . . . .

The motor controller 1705 may be in communication with the processor 110. The communication may be analog or digital. The processor 110 controls the movement of the shaft 1810 (and thus the angle of the mirror face 1800) (via the motor controller 1705) and the timing of the frame bias commands for the frame(s). In accordance with aspects of the disclosure, the angle of the mirror face 1800 is controlled between the readout of the frames.

Figure 19:
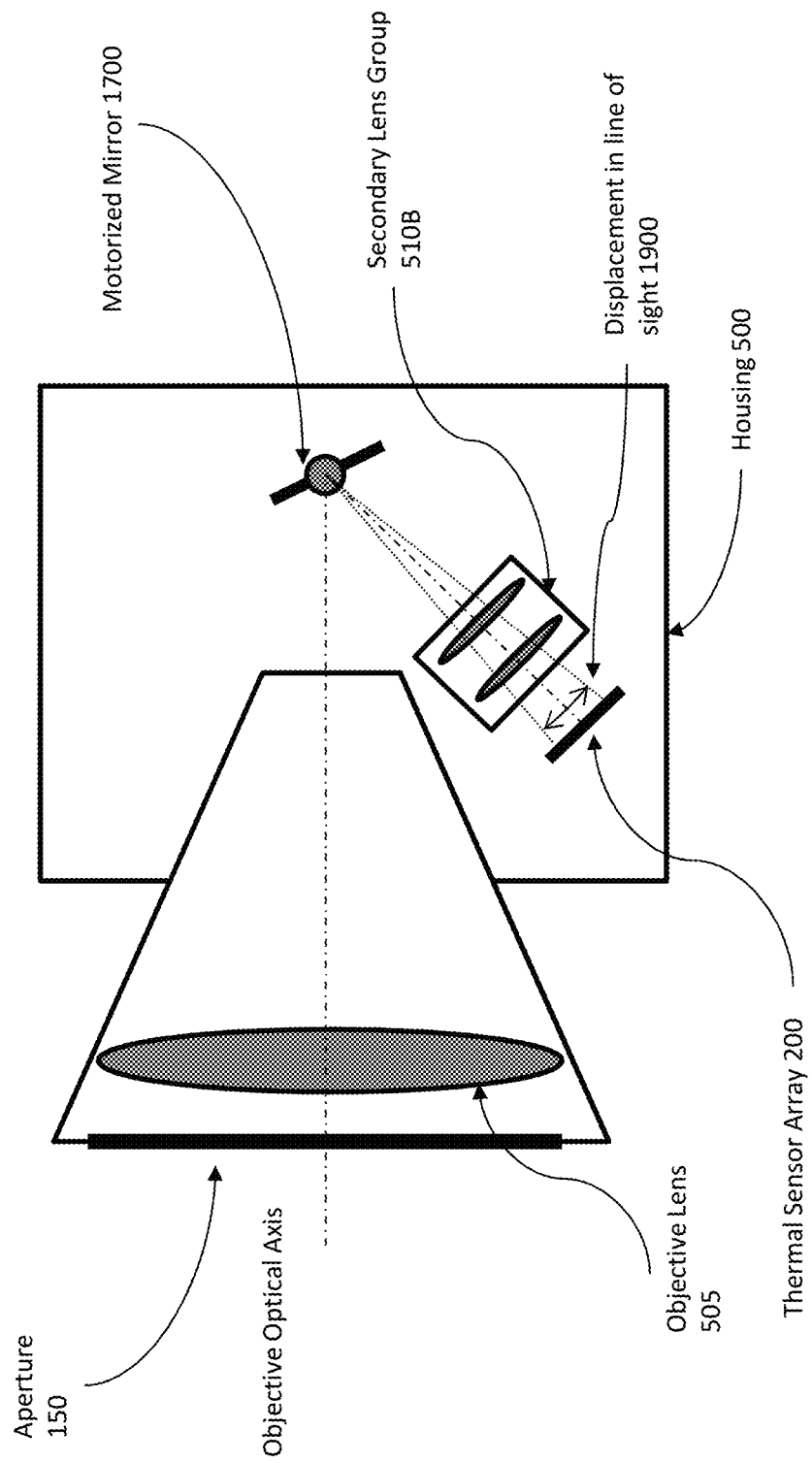
FIGS. 19 and 20 depicts sectional views of the system having the anti-detection mechanism of FIG. 17 in accordance with aspects of the disclosure showing different objective optics.
Figure 20:
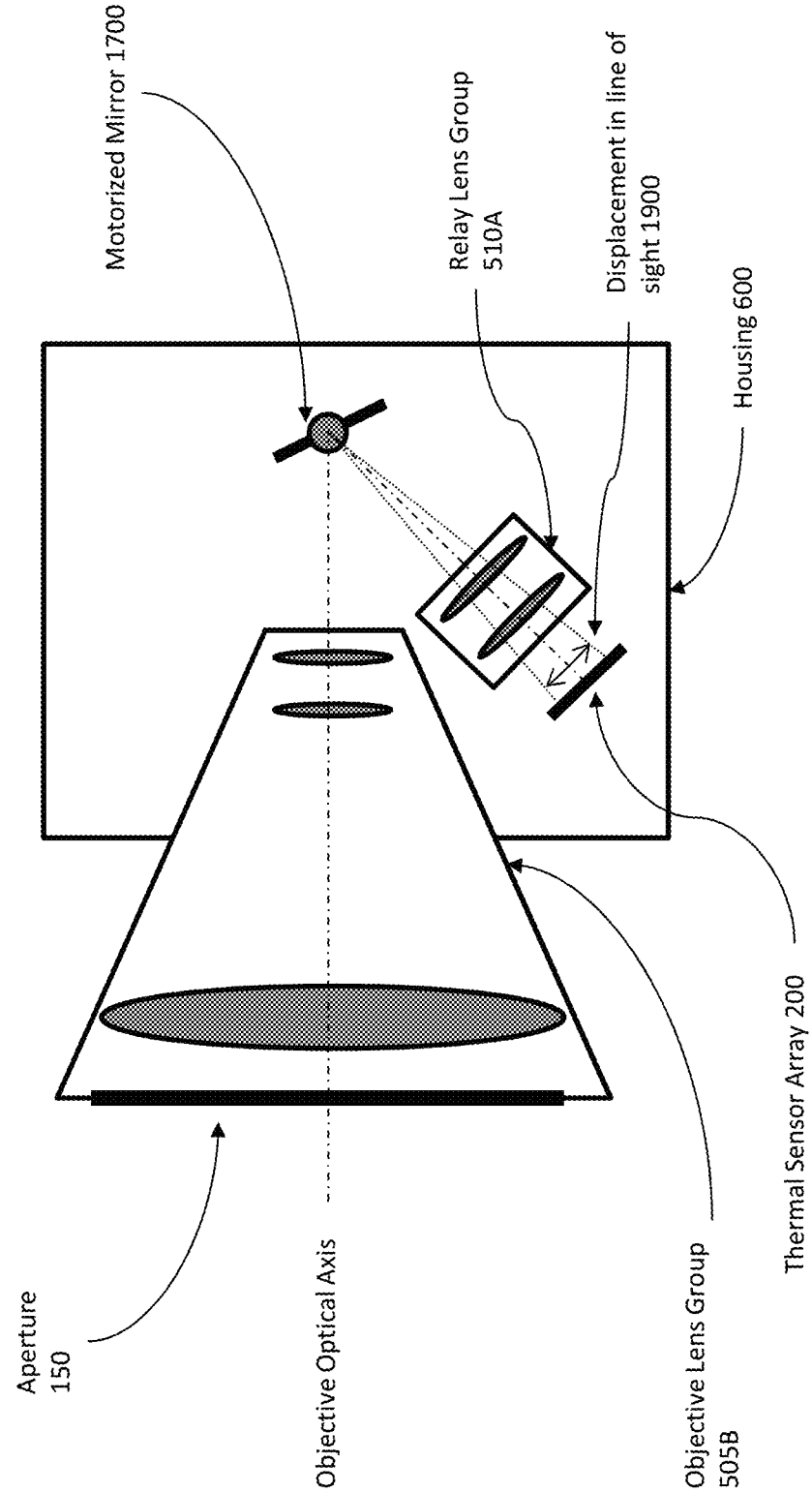

FIGS. 19 and 20 illustrate two different configurations for optics which may be used with the motorized motor 1700 in accordance with aspects of the disclosure. These figures depict sectional views of the system (housing). In both configurations, the motorized mirror 1700 is positioned at an angle with respect to the optical axis and the thermal sensor array 200. For example, in a home position (not rotated), the mirror face 1800 may be at a 45° with respect to the optical axis. In an aspects of the disclosure, the mirror face 1800 may rotate +−a maximum angle. The maximum angle may correspond to a certain percentage of the field of view. The maximum angle may be determined based on the size of the row on the thermal sensor array 200 and the distance between the mirror face 1800 and the thermal sensor array 200. For example, the angle may correspond to about 20% of the field of view. However, the maximum angle may change depending on the application for the thermal sensor array 200 (e.g., mission). For example for critical missions, the preset angle may be smaller such that a smaller field of view is impacted. The rotation of the mirror, causes a displacement in the line of sight 1900 at the thermal sensor array 200. The double arrows in FIGS. 19 and 20 show the linear displacement. The doted and dashed line represents the line of sight with no angular rotation, e.g., default angle or starting point. The dotted lines represent the maximum linear displacement and correspond to the maximum rotation angles.

In an aspect of the disclosure the thermal sensor array 200 is oriented such that simultaneous row reads are performed perpendicular to the mirror range of motion. As shown in FIGS. 19-20, the rows may be read top-left to bottom-right or vice versa.

In an aspect of the disclosure, the center of the mirror face 1800 may be aligned with the objective optical axis. In FIG. 19, the objective lens 500 and secondary lens group 510B focus the light at the thermal sensor array 200. The objective lens collects the target energy. The secondary lens group 510B focuses the light reflected by the motorized mirror 1700 onto the thermal sensor array 200. In FIG. 20, the objective lens group 500A also has a pupil relay. The objective lens group 500A collected the target energy (optical energy) and recollimates it. The objective lens group 500A re-images the pupil at the motorized mirror 1700 (mirror face 1800). By locating the pupil plane coincident with the motorized mirror 1700 (mirror face 1800), the optical distortions under mirror rotation(s) may be minimized.

In an aspect of the disclosure, the relationship between the rotation angle of the motorized mirror 1700 and the linear displacement in the line of sight 1900 may be determined during calibration. For example, the motorized mirror 1700 may be rotated to a specific angle and the linear displacement in the line of sight 1900 may be determined, e.g., number of rows. This determined linear displacement may be stored in memory in a look up table. The process may be repeated for a plurality of times to generate multiple correspondences. Each being stored in the memory in the look up table.

In other aspects of the disclosure, the relationship may be determined arithmetically. For example, the displacement is proportional to twice the rotation angle of the motorized mirror 1700 times the focal length of the secondary lens group 510B. Given a fixed pixel size, the number of displaced rows may be determined.

In accordance with aspects of the disclosure, the motorized mirror 1700 is rotated between the reading of frames.

Figure 21:
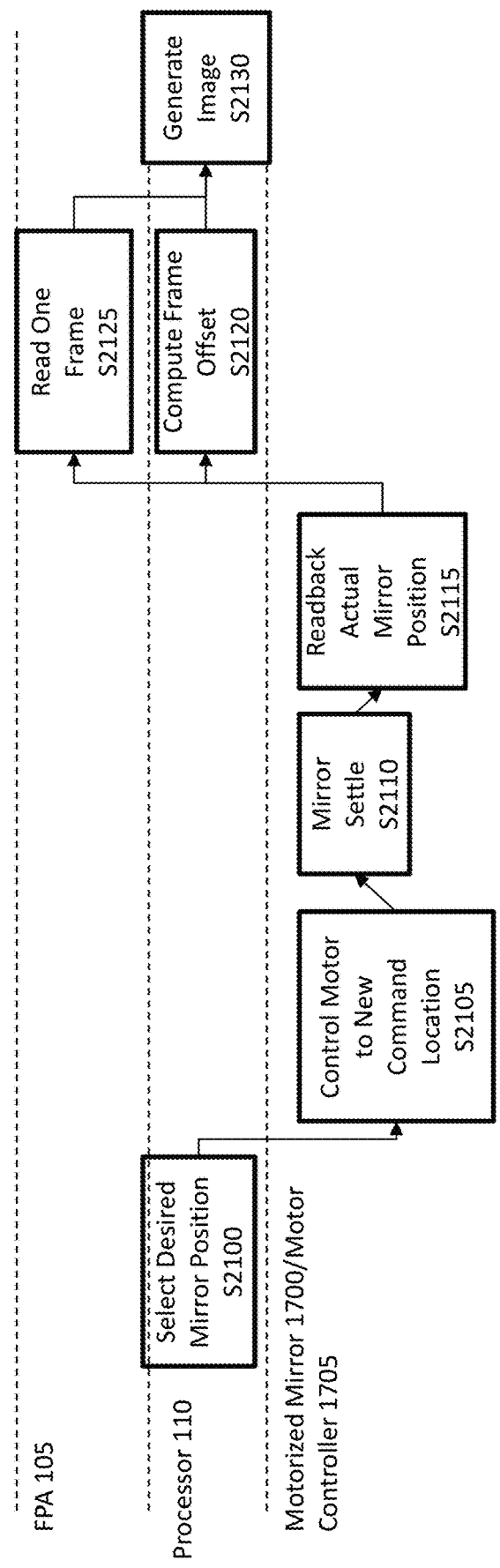
FIG. 21 depicts a flow for an anti-detection method in accordance with aspects of the disclosure.

FIG. 21 is a flow diagram of a method in accordance with aspects of the disclosure. At S2100, the processor 110 determines a desired angular position for the motorized mirror 1700. In an aspect of the disclosure, the desired angular position may be randomly determined within the +−maximum angular deflection. In other aspects of the disclosure, there may be a preset rotation pattern based on the number of frames. For example, between the first and second frame, the motorized mirror 1700 may be rotated to +0.1 degrees (from the baseline angle) and between the second and third frame, the motorized mirror 1700 may be rotated to −5.1 degrees (from the baseline angle), and between the third and fourth frame, the motorized mirror may be rotated to −5.1 degrees (from the baseline angle), e.g., no rotation. Thus, the pattern may include no rotation between some of the frames. Additionally, the pattern may include different rotations between each frame. In other aspects, the pattern may repeat certain rotations between frames. For example, the rotation between the tenth and eleventh frame may be to +2.2 degrees (from baseline) and the rotation between the twentieth and twenty-first frame may also be to +2.2 degrees, e.g., same rotations every 10th frame.

Once the processor 110 determines the desired angular position, the processor 110 transmits a command to the motor controller 1705. At S2105, the motor controller 1705 controls the motorized mirror 1700 to rotate to the desired angular position. The manner which the motor controller 1705 controls the motorized mirror 1700 will be based on the type of motor in the motorized mirror 1700.

At S2110, the system waits for the motorized mirror 1700 to settle into the desired angular position. AS2115, the position of the motorized mirror 1700 (mirror face 1800) is determined using a rotary encoder 1820. In an aspect of the disclosure, the motor controller 1705 determines the actual angular position using the output of the rotary encoder 1820 to ensure that the motorized mirror 1700 (mirror face 1800) is at the desired angular position (commanded angular position). In an aspect of the disclosure, the processor 110 also determines the actual angular position using the output of the rotary encoder 1820. In other aspects, the motor controller 1705 transmits the determined actual angular position to the processor 110.

At S2120, the processor 110 determines the linear displacement in the line of sight 1900 using the determined actual angular position, e.g., frame offset. As described above, this determination may include using a look up table in memory. For example, the processor 110 may retrieved the look up table from memory and determine the line displacement, e.g., number of rows displaced, from the look up table, which corresponds to the determined actual angular position. Also, instead of using the look up table, the processor 110 may calculate the linear displacement in a manner described above. Then the processor 110 may calculate the number of rows by dividing the linear displacement by the row size (pixel size).

The processor 110 issues frame command, row command(s) and current offsets for the row(s) to the FPA 105 (to the ROIC).

At 2125, the FPA 105 reads one frame of the detection target 500 and generates the image data for each row. In an aspect of the disclosure, the number of the rows within a frame that is readout may be different due to the rotation. For example, when the motorized mirror 1700 is rotated to a maximum angle, e.g., +maximum, the number of rows readout may be less than when the motorized mirror is rotated to the baseline.

The FPA 105 (ROIC) transmits the image data for each row (commanded row) to the processor 110. At 2130, the processor 110 generates the image for display.

Figure 22:
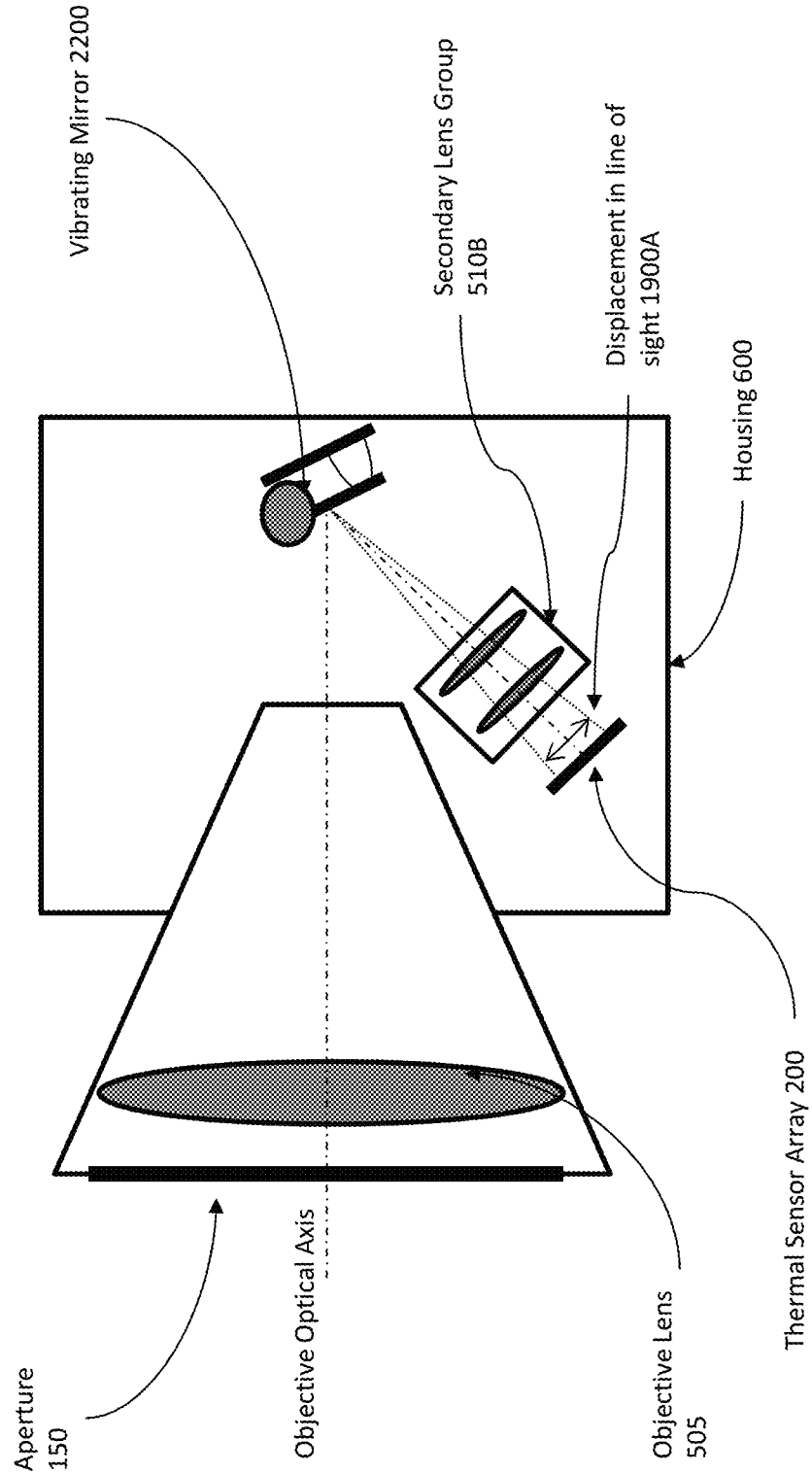
FIG. 22 depicts a section view of a system having another anti-detection mechanism in accordance with aspects of the disclosure.

In other aspects of the disclosure, instead of using a motorized mirror 1700 and a motor controller 1705, a vibrating mirror 2200 may be used. The vibrating mirror 2200 may be positioned in the same location as the motorized mirror 1700 as shown in FIG. 22. For example, the vibrating mirror 2200 may be located at any position along the optical path between the optics 505, 510. However, in other aspects, the vibrating mirror 2200 may be located at a pupil focal point. The mirror face may rotate with respect to a rotation axis. This rotation causes the image on the thermal sensor array 200 to be linearly translated. The angle of rotation is due to external stimulus on the system (e.g., housing 600. This external stimulus may be different depending where the system is mounted or located. For example, the external stimulus may be due to moving of a vehicle that the system is mounted to, e.g., car, truck, airplane, etc. The external stimulus may also be due to a person carrying the system moving.

The vibrating mirror 2200 may also be used in the optical configurations shown in FIGS. 19 and 20.

Figure 23:
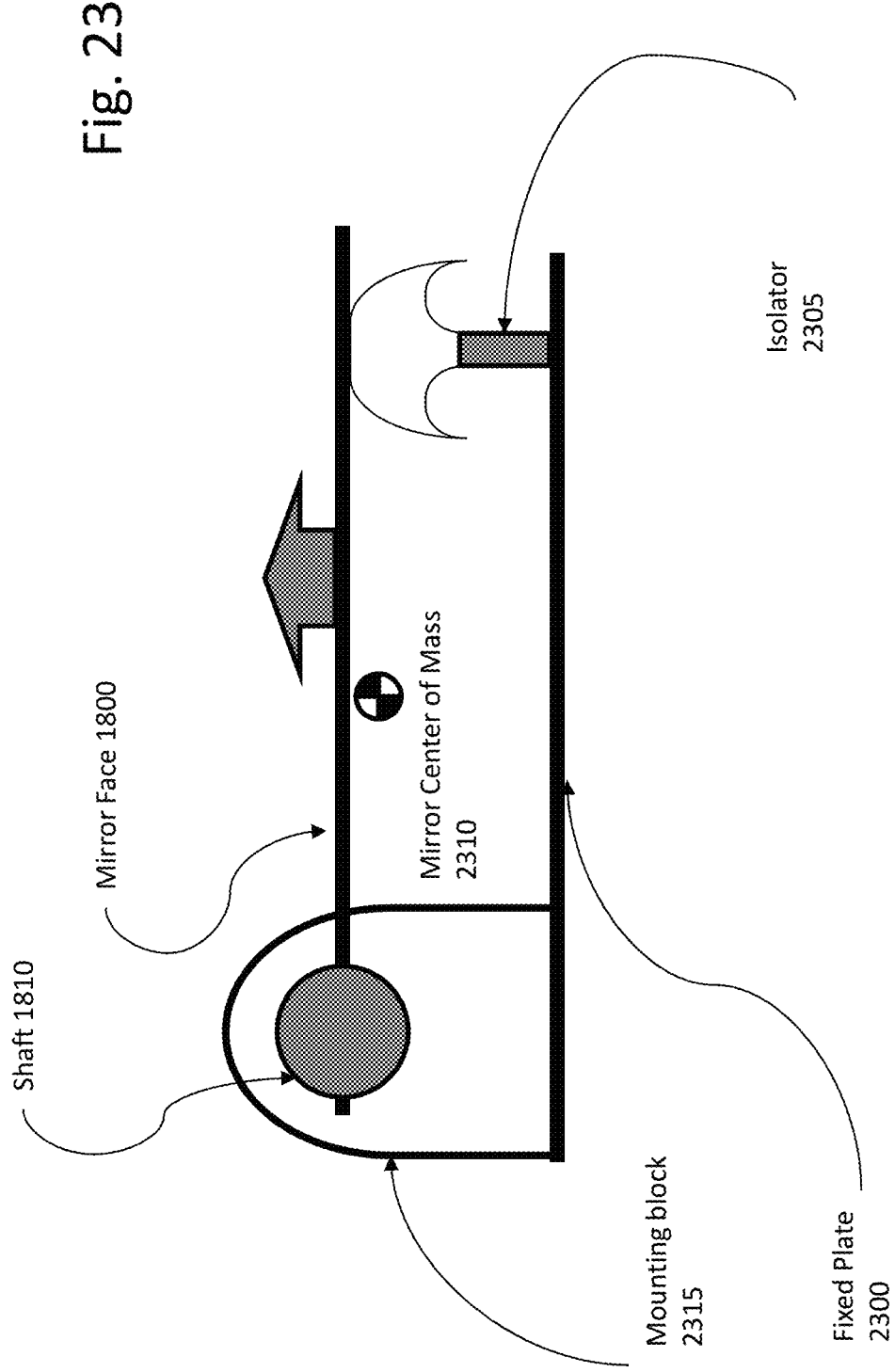
FIG. 23 depicts a view of certain components of an example of the anti-detection mechanism in FIG. 22 in accordance with aspects of the disclosure.

FIG. 23 illustrates a diagram of certain components of the vibrating mirror 2200 in accordance with aspects of the disclosure. The vibrating mirror 2200 may include the mirror itself (face 1800), an isolator 2305, a fixed plate and shaft 1810 and a mounting block 2315. The fixed plate 2300 may be a projection from the housing 600. The fixed plate 2300 may also be a portion of the housing. The isolator 2305 is mounted to the fixed plate 2300 (on one end). The other end of the isolator 2305 is attached to the mirror. This enables the mirror to rotate when an external stimulus is applied. The mirror has a center of mass 2310 (COM). The shaft 1810 is offset from the center of mass 2310 to allow for torque. The mounting block 2315 may be positioned on the sides of the mirror. The mounting block 2315 is mounted to the fixed plate 2315. In an aspect of the disclosure, each mounting block 2315 may include rotary bearings similar to shown in FIG. 18.

The mounting block 2315 may also include a rotary encoder 1820 (not shown in FIG. 23) configured to detect the position of the shaft. In other aspects of the disclosure, a RPM speed sensor may be used to determine the speed of the shaft. The shaft may be a split shaft similar to shown in FIG. 18.

The isolator may selected to achieve a maximum spreading of any emitted signal during readout but at the same time meet a blur requirement for the imaging.

An expected angular change over a time interval t is:

$$\phi = \int \tau \cdot \text{sinc}\left(\frac{\omega \cdot \tau}{2}\right) \cdot H(j\omega) \cdot D(j\omega) \delta\omega \tag{1}$$

where H(jω) is a transfer function, and D(jω) is an external stimulus.

Thus, the isolator 2305 may be selected such that φ is maximized at τ equal to the desired maximum integration time allowed to the detecting system but subject to a constraint that φ less than 1 pixel instantaneous field of view (IFOV) at τ equal to the sensor frame time. The mounting location with respect to the mirror also impacts the transfer function.

The excitation force may be parameterized as a power spectral distribution, a functional description of random forces with amplitudes dependent on frequency. The forces may be transmitted to a mirror through one or more isolators 2305 (one is shown in FIG. 23) and a rotary bearing. Transmissibility differences between the rotary bearing and one or more isolators 2305 creates a torque imbalance. The coupling of a translational disturbance to a rotation of the mirror is a (typically second order) differential equation.

For a single isolator the transfer function is $$H(j\omega) = \frac{s_0 - (s - s_0)T(j\omega)}{I \cdot j\omega} \quad (2)$$

where s is the distance between the isolator 2305 and the shaft, $s_0$ is the distance between the shaft and the COM, I is the mirror moment of inertia and T(jω) is the frequency domain transmissibility function of the isolator 2305.

Certain vendors provide the transmissibility function of the isolator 2305 (curve) in the spec sheet. This accounts for non-linearities in the design. Other vendors provide parameters which may be used to calculate the transmissibility curve. The transmissibility function may be calculated by:

$$T(f) = \left| \frac{1}{(j \cdot f)^2 + 2(j \cdot f)\eta f_N + (f_N)^2} \right| \quad (3)$$

where ($f_N$) is the natural frequency and η is the damping coefficient.

The transmissibility function may be calculated by:

$$T(f) = \left| \frac{1}{m(j \cdot f)^2 + c(j \cdot f) + k} \right| \quad (4)$$

where k is the spring constant, c is the damping coefficient and m is the nominal load mass. Different types of isolators may be used. For example, a thin bell or grommet style isolator may be used. However, in other aspects, a strut may be used. Depending on the size of the system, the strut may be connected to the mirror via an intermediary.

Figure 24:
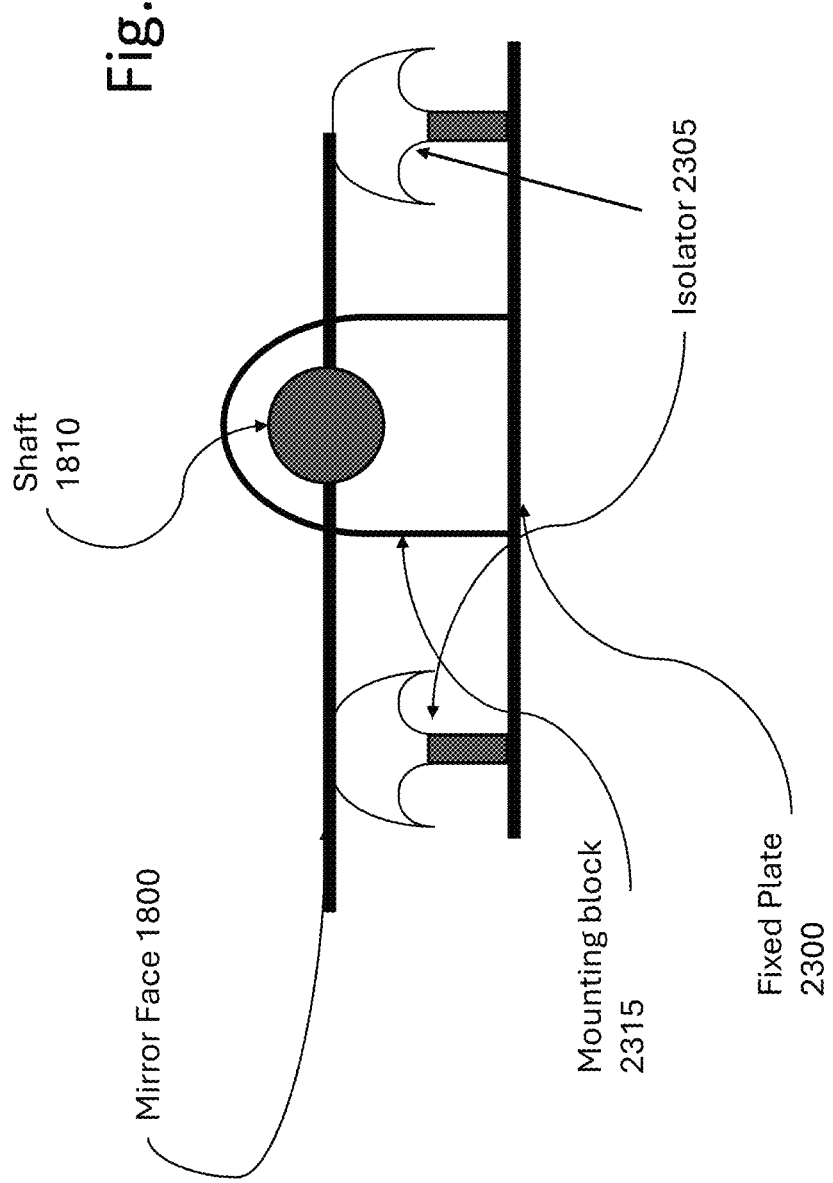
FIG. 24 depicts a view of certain components of another example of the anti-detection mechanism in FIG. 22 in accordance with aspects of the disclosure.

In other aspects of the disclosure, multiple isolators 2305 may be used such as two isolators. FIG. 24 isolates a diagram of certain components of the vibrating mirror 2200 in accordance with aspects of the disclosure with two isolators. Here, the shaft 1810 may be located at the COM and the isolators 2305 are located at the ends of the mirror. In order for the mirror face 1800 to rotate, the transmissibility function (curve) for the different isolators should be different.

The transfer function for the two isolators 2305 is:

$$H(j\omega) = \frac{s_1 \cdot T_1(j\omega) - s_2 \cdot T_2(j\omega)}{I \cdot j\omega} \quad (5)$$

where $s_1$ is the distance between one of the isolators and the shaft and $s_2$ is the distance between the other isolator and the shaft, $T_1(j\omega)$ is the transmissibility function of the isolator and $T_2(j\omega)$ is the transmissibility function of the other isolator, I is the mirror moment of inertia.

In other aspects, the selected isolator(s) 2305 may be based on the expected external stimulus. For example, there may be a different isolator where the system is handheld verses mounted on a vehicle.

In an aspect of the disclosure, the selected isolator may also be based on a desired maximum linear displacement over an expected external stimulus. This is because if the mirror face 1800 is allowed to rotate with a large change of angles, too much of the field of view may be impacted.

In an aspect of the disclosure, the relationship between the angle of the vibrating mirror 2200 and the linear displacement in the line of sight 1900A may be determined during calibration. For example, an external stimulus may be exerted on the system, the mirror angle determined and the linear displacement in the line of sight 1900A may be determined, e.g., number of rows. This determined linear displacement may be stored in memory in a look up table. The process may be repeated for a plurality of times to generate multiple correspondences. Each being stored in the memory in the look up table.

In other aspects of the disclosure, the relationship may be determined arithmetically in a similar manner as described above.

Figure 25:
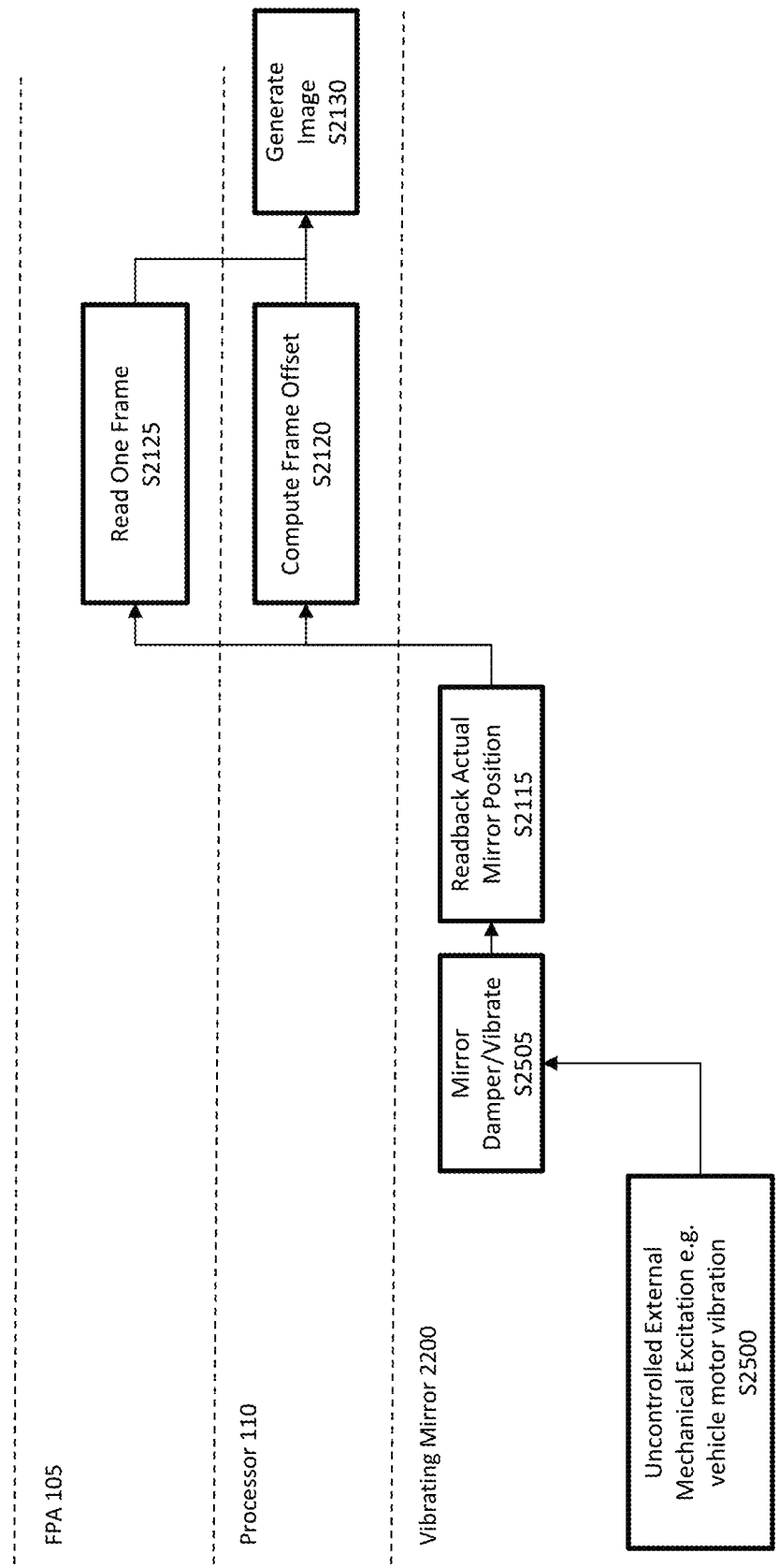
FIG. 25 depicts a flow for an anti-detection method in accordance with aspects of the disclosure.

FIG. 25 is a flow diagram of a method in accordance with aspects of the disclosure. At 2500, an external stimulus (mechanical excitation) is received by the system. As noted above, this stimulus may be due to a vehicle vibrating or a person moving. At S2505, the isolator(s) 2305 damping the vibrations and transfer the stimulus to the mirror face 1800.

When it is time to read one frame of the detection target 500, the processor 110 via the encoder determines the mirror position, e.g., angular position. This position may be the same as a prior position if no stimulus is applied. However, the position may change due to the stimulus and damping. In an aspect of the disclosure, the actual mirror position may be determined periodically at the frame readout rate. In this aspect, just prior to issuing the frame command to the FPA 105, the processor 110 determines the position. In other aspects, the processor 110 may determine the position at the same time as issuing the frame command to the FPA 105 (e.g., in parallel). In other aspects of the disclosure, the processor 110 may determine the position of the mirror when it receives the image data for a frame from the FPA 105.

At S2120, the processor 110 determines the linear displacement in the line of sight 1900A using the determined angular position, e.g., frame offset. As described above, this determination may include using a look up table in memory. For example, the processor 110 may retrieved the look up table from memory and determine the line displacement, e.g., number of rows displaced, from the look up table, which corresponds to the determined position. The processor 110 issues frame command, row command(s) and current offsets for the row(s) to the FPA 105 (to the ROIC).

At 2125, the FPA 105 reads one frame of the detection target 500 and generates the image data for each row. In an aspect of the disclosure, the number of the rows within a frame that is readout may be different due to the rotation.

The FPA 105 (ROIC) transmits the image data for each row (commanded row) to the processor 110. At 2130, the processor 110 generates the image for display.

Figure 26:
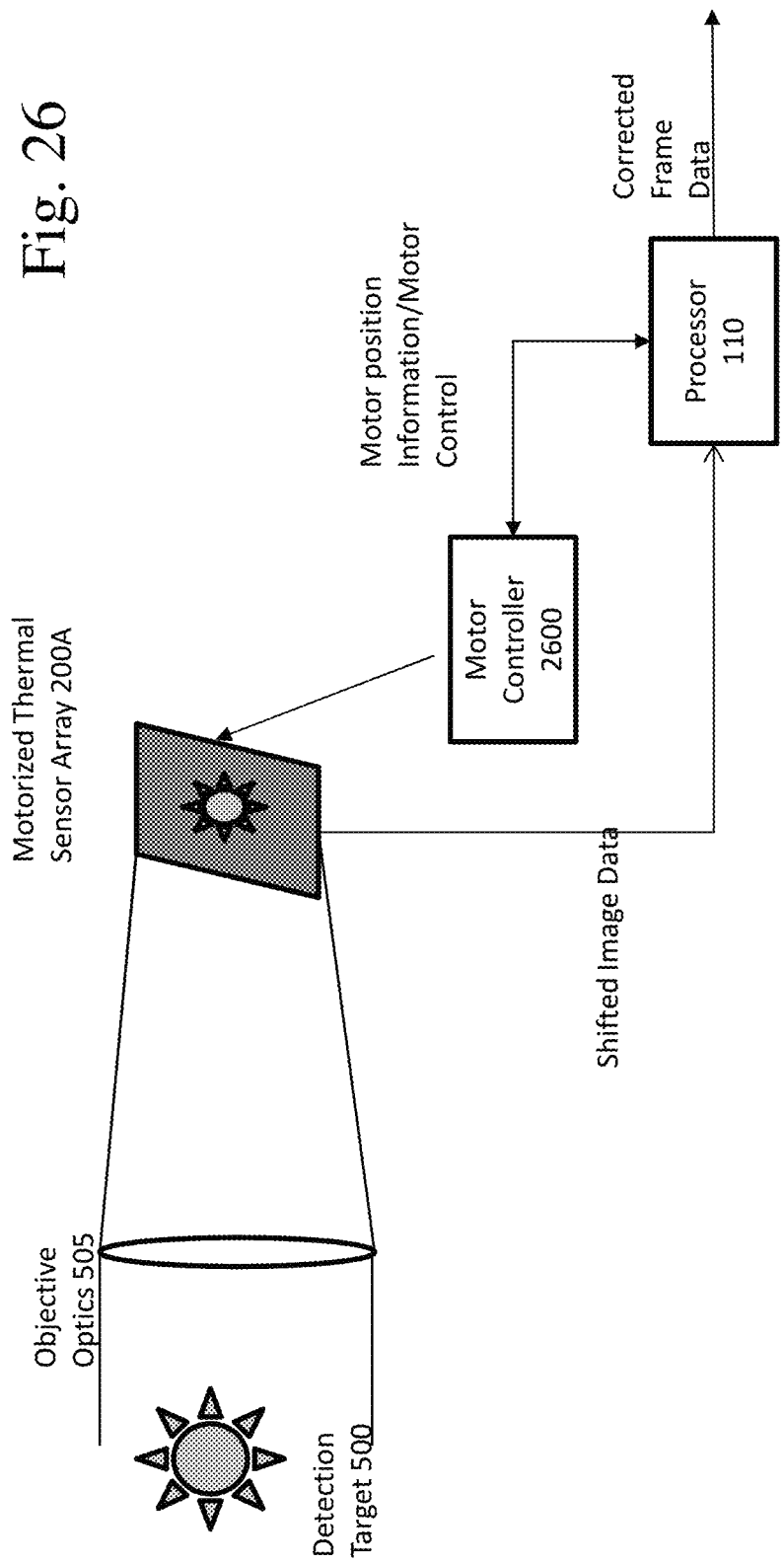
FIG. 26 depicts anti-detection mechanism in the system in accordance with aspects of the disclosure using a motorized thermal sensor array.
Figure 31:
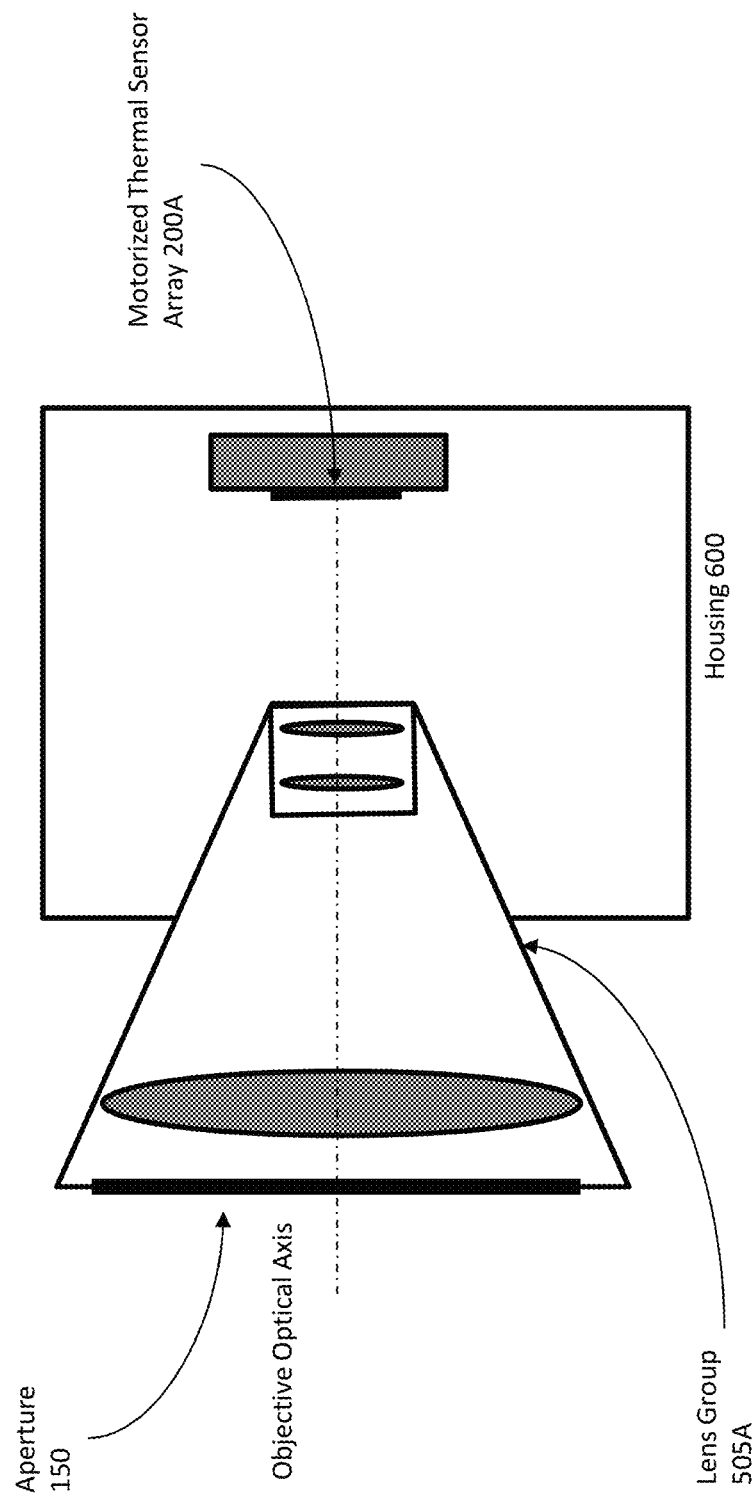
FIG. 31 depicts a section view of a system having a motorized thermal sensor array in accordance with aspects of the disclosure.

In other aspects of the disclosure, the mirror (either motorized mirror 1700 or vibrating mirror 2200) may be omitted. Instead, the thermal sensor array 200 may be linearly moved. In an aspect of the disclosure, the array 200 may be motorized, e.g., a motorized thermal sensor array 200A. FIG. 26 illustrates a diagram showing components of an anti-detection mechanism including a motorized thermal sensor array 200A in accordance with aspects of the disclosure. The motorized thermal sensor array 200A may be aligned with the objective axis as shown in FIG. 31. The motorized thermal sensor array 200A may be positioned in the same location as the motorized mirror 1700 or the vibrating mirror 2200. The distance between the objective optics 505 may be based on the focal length of the lens. The motorized thermal sensor array 200A moves linearly and perpendicular to the objective optical axis. The movement of the thermal sensor array 200A is also perpendicular to a readout row (in the readout direction as shown in FIG. 4.

Figure 27:
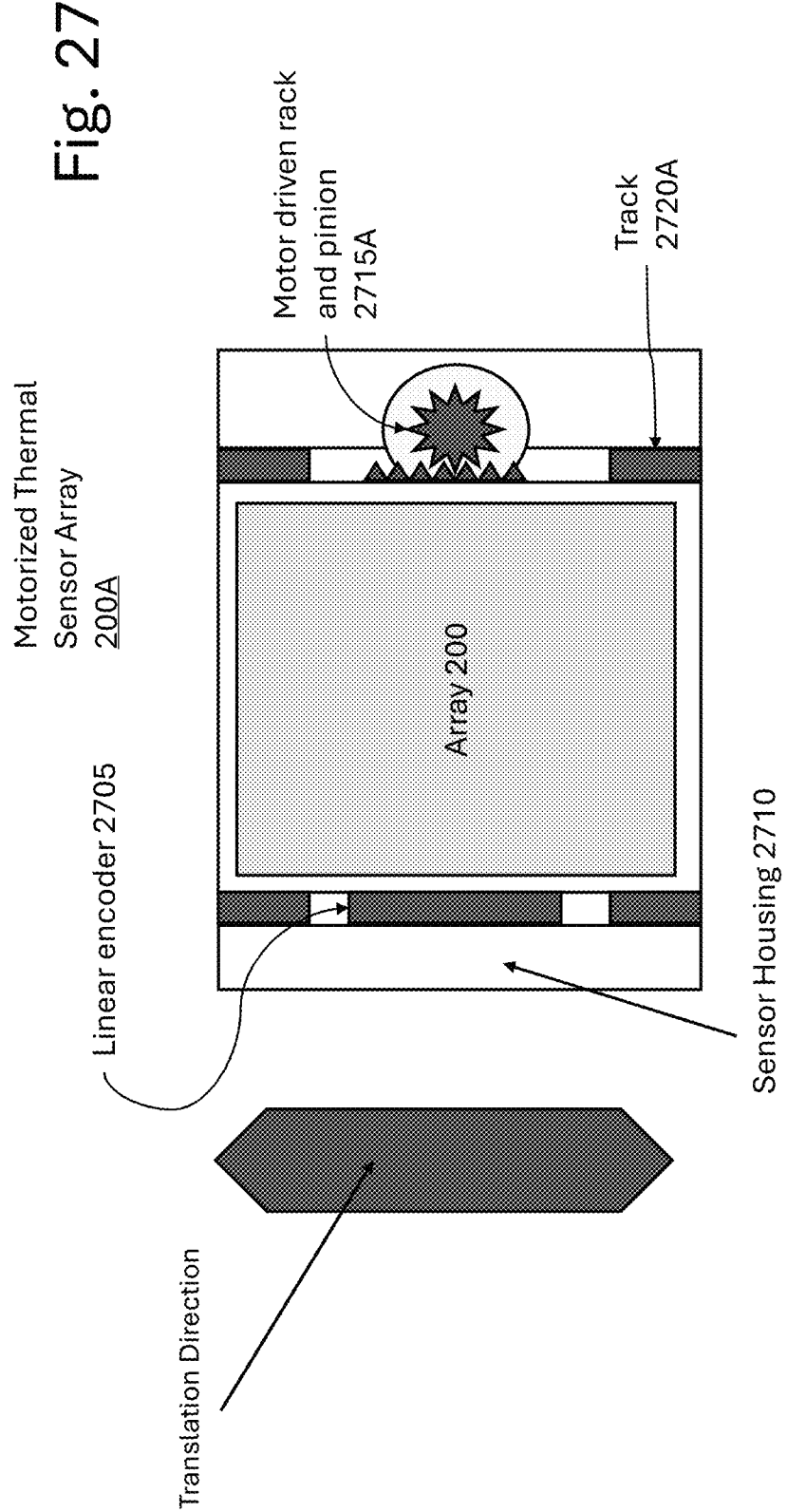
FIGS. 27 and 28 depicted views of an example of a motorized thermal sensor array in accordance with aspects of the disclosure.
Figure 28:
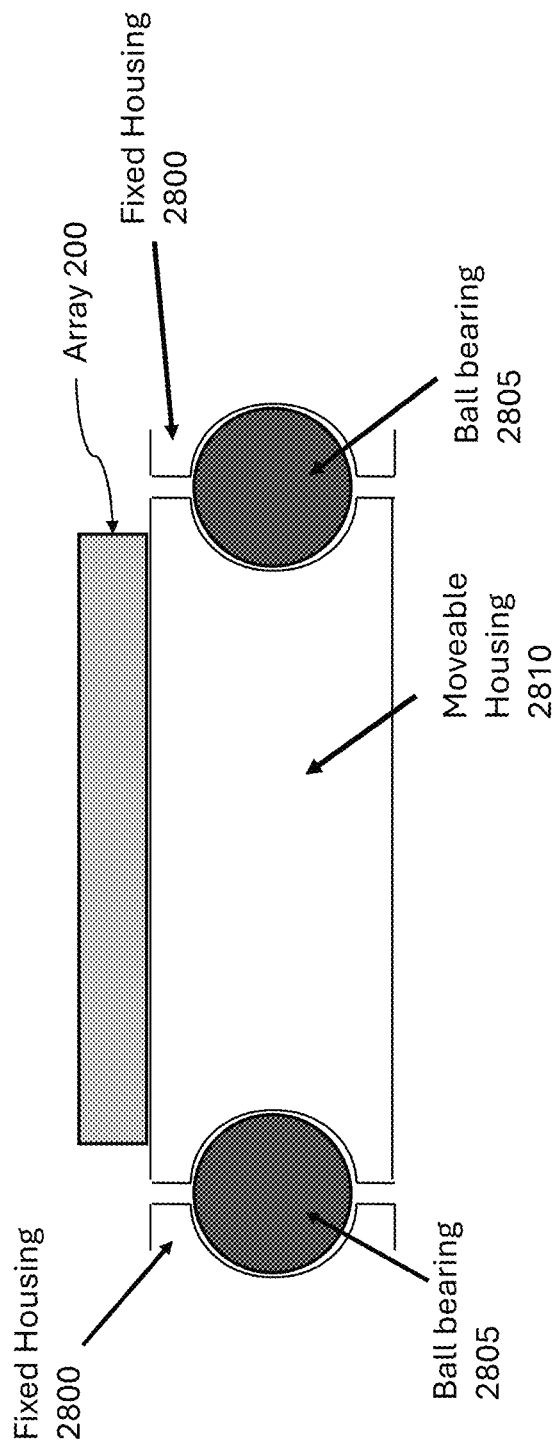

FIGS. 27 and 28 illustrate different views of an example of a motorized thermal sensor array 200A in accordance with aspects of the disclosure. The array 200 is mounted on a sensor housing 2710. The sensor housing comprises two portions a fixed housing 2800 and a moveable housing 2810. The moveable housing 2810 moves relative to the fixed housing 2800. The fixed housing 2800 may be mounted to the housing 600. A track 2720A is located between the fixed housing 2800 and moveable housing 2810. The track 2720A enables the movement in a single dimension. The track 2720A includes bearings such as ball bearings 2805. The motorized thermal sensor array 200A may also include a rack and pinion 2715A driven by a motor (not shown). The rack may be attached to the moveable housing 2810. The rack may only extend on a portion of the housing to limit the amount of movement. Additionally, the track 2720A may only extend a portion of the housing to limit the amount of movement.

In an aspect of the disclosure, the motorized thermal sensor array 200A move within a preset maximum, which corresponds to a certain percentage of the field of view. For example, the maximum movement may correspond to about 20% of the field of view. However, the maximum movement may change depending on the application for the thermal sensor array 200A (e.g., mission). For example for critical missions, the preset maximum may be smaller such that a smaller field of view is impacted.

The pinion may be attached to a rotary motor. The rotary motor may be an AC motor. The motor controller 2600 may be an AC motor controller. The AC motor controller may produce one or more commands to the rotary motor causing the motor to rotate the pinion which is turn causes the moveable housing 2810 to move on the rack in the track 2720A. In an aspect of the disclosure, the motor control may be implemented using a closed loop control. For example, the linear encoder 2705 may sense the position and compute an error and modulates the electrical power to generate a motor power signal in accordance with the motor type and control, to the rotary motor. In other aspects, the motor may be a brush or brushless DC motor. The motor controller 2600 may be a DC motor controller.

The modulation of the motor power signal may vary based on the motor type and may be a pulse-width modulation (PWM), a variable DC level, variable amplitudes one or more AC signals or parallel pulses. The motor controller 2600 is supplied with electrical power (not shown) needed to supply the modulated motor power signal.

Figure 29:
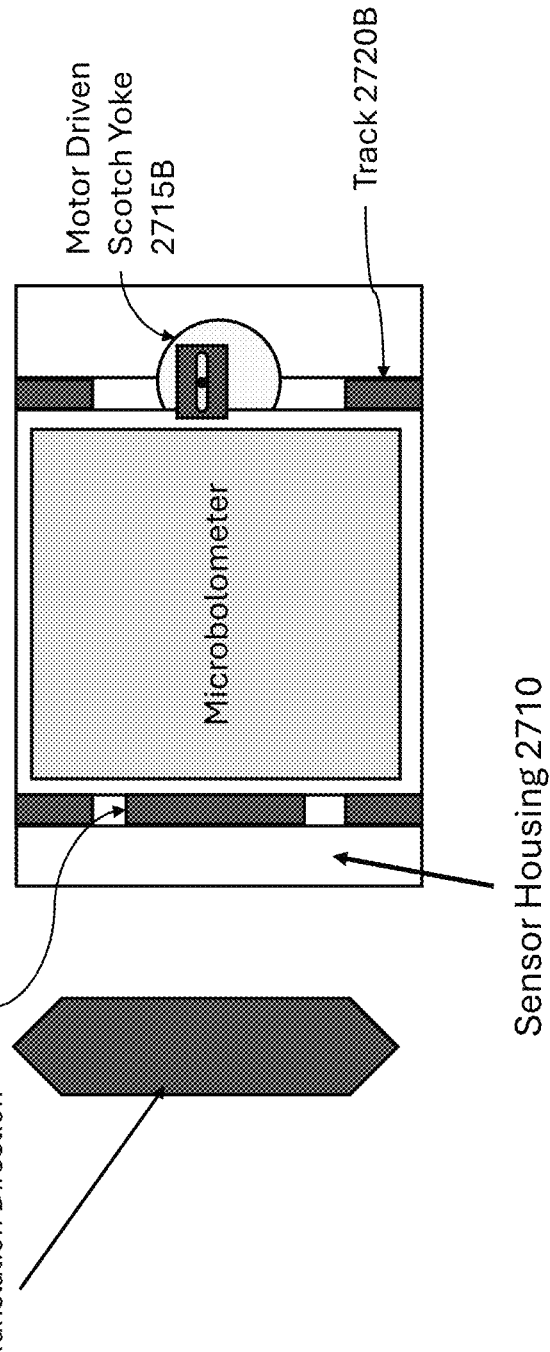
FIGS. 29 and 30 depicted views of another example of a motorized thermal sensor array in accordance with aspects of the disclosure.
Figure 30:
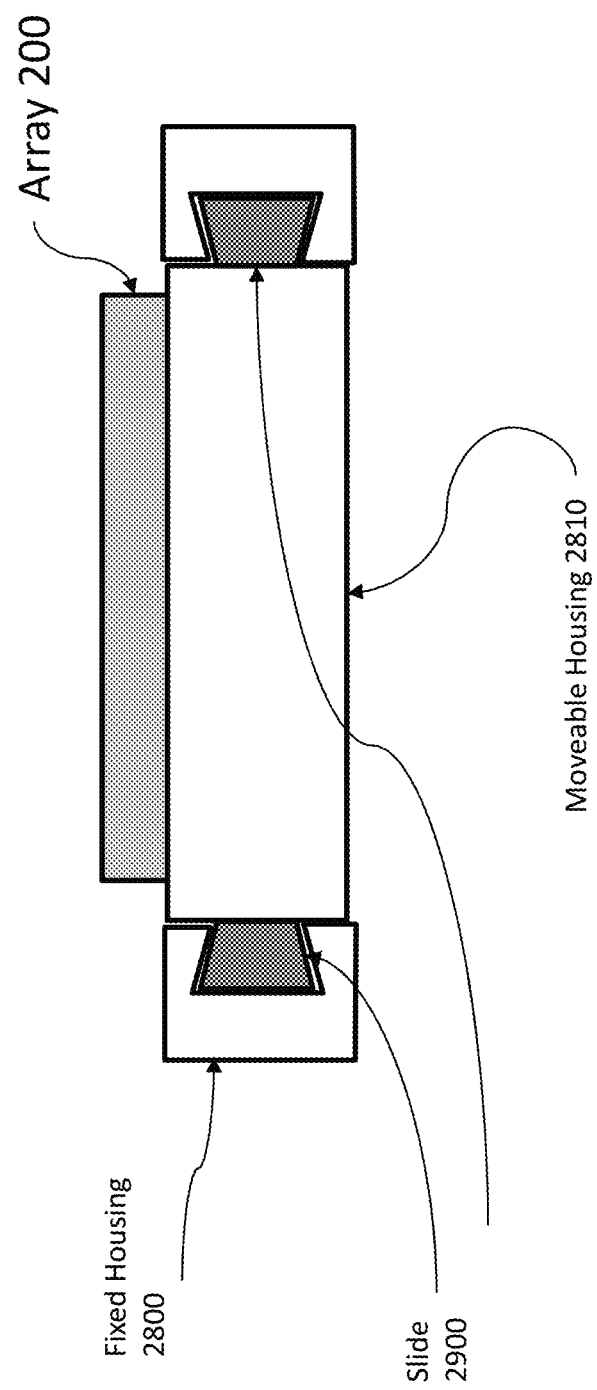

FIGS. 29 and 30 illustrate different views of another example of a motorized thermal sensor array 200B in accordance with aspects of the disclosure.

The differences between the motorized thermal sensor array 200B and 200A is the driving mechanism and track 2720B. The driving mechanism includes a scotch yoke driven by a rotary motor. The yoke is connected to the rotary motor. The piston and spring may be in contact with a slider (slide 2900). The slide is located with the track 2720B. The slides 2900 may be located in the corners of the track. The slide length is proportional to the linear movement. In an aspect of the disclosure, the slide 2900 does not extend the full length of the array 200.

In other aspects of the disclosure, instead of a rotary motor, a linear motor may be used. The linear motor may be attached to a projection extending from the moveable housing 2810. In other aspects of the disclosure, the movement may be driven by a piezoelectric device. The piezoelectric drive may be a DC device.

In an aspect of the disclosure, the relationship between the linear movement of the motorized thermal sensor array 200A/200B and the linear displacement in the image may be determined during calibration. For example, the motorized thermal sensor array 200A may be movement by a known distance and the linear displacement may be determined, e.g., number of rows. This determined linear displacement may be stored in memory in a look up table. The process may be repeated for a plurality of times to generate multiple correspondences. Each being stored in the memory in the look up table.

In other aspects, the relationship may be calculated based on the pixel size and displacement. For example, if the pixel size is 12 µm and the displacement is 60 µm, the offset is 5 pixels. Thus, the offset is determined by dividing the displacement by the pixel size (D/P), where D is the displacement and P is the pixel size.

In accordance with aspects of the disclosure, the motorized thermal sensor array 200A/200B is moved between the reading of frames (linear movement).

Figure 32:
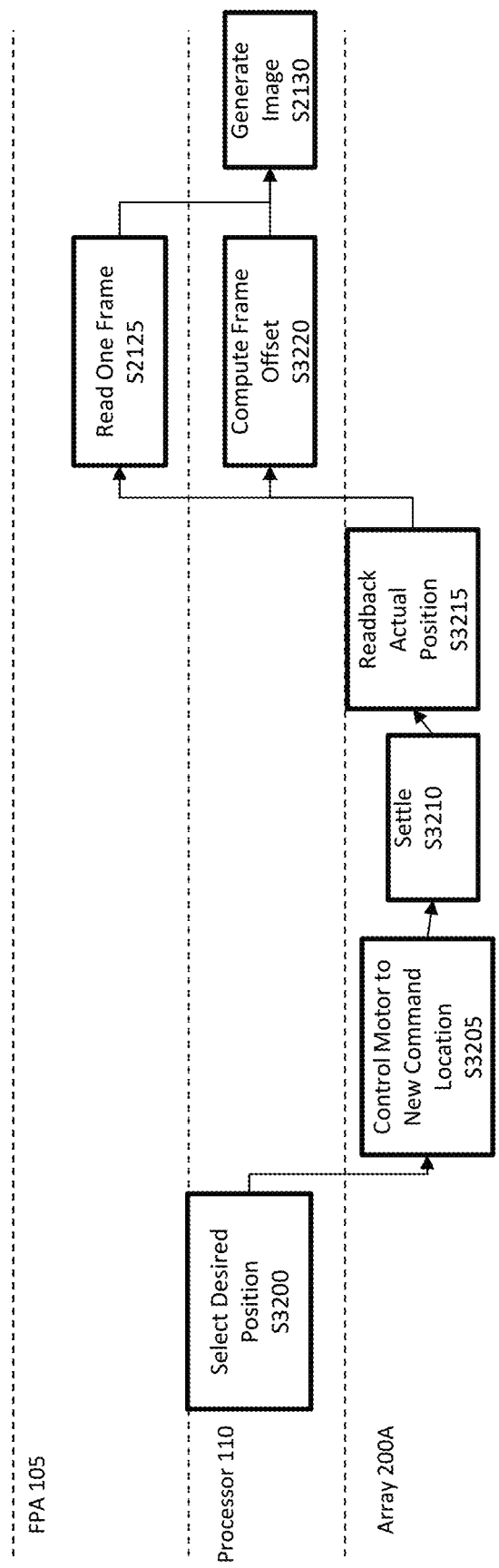
FIG. 32 depicts a flow for an anti-detection method in accordance with aspects of the disclosure.

FIG. 32 is a flow diagram of a method in accordance with aspects of the disclosure. At S3200, the processor 110 determines a desired position for the motorized thermal sensor array 200A/200B. This determination may occur at the frame rate. In an aspect of the disclosure, the desired position may be randomly determined within the +−maximum linear translation. In other aspects of the disclosure, there may be a preset translation pattern based on the number of frames. For example, between the first and second frame, the motorized thermal sensor array 200A/200B may be translated by 0.15 mm (from a baseline position) and between the second and third frame, the motorized thermal sensor array 200A/200B may be translated to −0.45 mm (from the baseline), and between the third and fourth frame, the motorized thermal sensor array 200A/200B may be translated to −0.45 mm (from the baseline), e.g., no movement. Thus, the pattern may include no movement between some of the frames. Additionally, the pattern may include different movements between each frame. In other aspects, the pattern may repeat certain movement (translations) between frames. For example, the translation between the tenth and eleventh frame may be to +0.25 mm (from baseline) and the rotation between the twentieth and twenty-first frame may also be to +0.25 mm, e.g., same movement every $10^{th}$ frame. The baseline may be centered with respect to the objective axis.

Once the processor 110 determines the desired position, the processor 110 transmits a command to the motor controller 2600. At S3205, the motor controller 2600 controls the motorized thermal sensor array 200A/200B to move to the desired position. The manner which the motor controller 2600 controls the motorized thermal sensor array 200A/200B will be based on the type of motor in the motorized thermal sensor array 200A/200B.

At S3210, the system waits for the motorized thermal sensor array 200A/200B to settle into the desired position. AS3215, the position of the motorized thermal sensor array 200A/200B is determined using a linear encoder 2705. In an aspect of the disclosure, the motor controller 2600 determines the actual angular position using the output of the linear encoder 2705 to ensure that the motorized thermal sensor array 200A/200B is at the desired position (commanded position). In an aspect of the disclosure, the processor 110 also determines the actual position using the output of the linear encoder 2705. In other aspects, the motor controller 2600 transmits the determined actual position to the processor 110.

At S3220, the processor 110 determines the linear displacement in the image using the determined actual position, e.g., frame offset. As described above, this determination may include using a look up table in memory. For example, the processor 110 may retrieved the look up table from memory and determine the line displacement, e.g., number of rows displaced, from the look up table, which corresponds to the determined actual position. Also, instead of using the look up table, the processor 110 may calculate the linear displacement in a manner described above. Then the processor 110 may calculate the number of rows (offset) by dividing the linear displacement by the row size (pixel size), e.g., D/P.

The processor 110 issues frame command, row command(s) and current offsets for the row(s) to the FPA 105 (to the ROIC).

At 2125, the FPA 105 reads one frame of the detection target 500 and generates the image data for each row. In an aspect of the disclosure, the number of the rows within a frame that is readout may be different due to the linear movement of the motorized thermal sensor array 200A/200B. For example, when the motorized thermal sensor array 200A/200B is move to a maximum translation, e.g., +maximum, the number of rows readout may be less than when the motorized thermal sensor array 200A/200B is not moved.

The FPA 105 (ROIC) transmits the image data for each row (commanded row) to the processor 110. At 2130, the processor 110 generates the image for display. \

In other aspects of the disclosure, instead of using the motorized thermal sensor array 200A/200B and a motor controller 2600, a vibrating thermal sensor array 200D may be used. The vibrating thermal sensor array 200B may be positioned in the same location as the motorized thermal sensor array 200A/200B as shown in FIG. 31. The vibrations of the vibrating thermal sensor array 200D may due to external stimulus on the system (e.g., housing 600). This external stimulus may be different depending where the system is mounted or located. For example, the external stimulus may be due to moving of a vehicle that the system is mounted to, e.g., car, truck, airplane, etc. The external stimulus may also be due to a person carrying the system moving. The vibrations translate the array 200D and thus the image detected.

Figure 33:
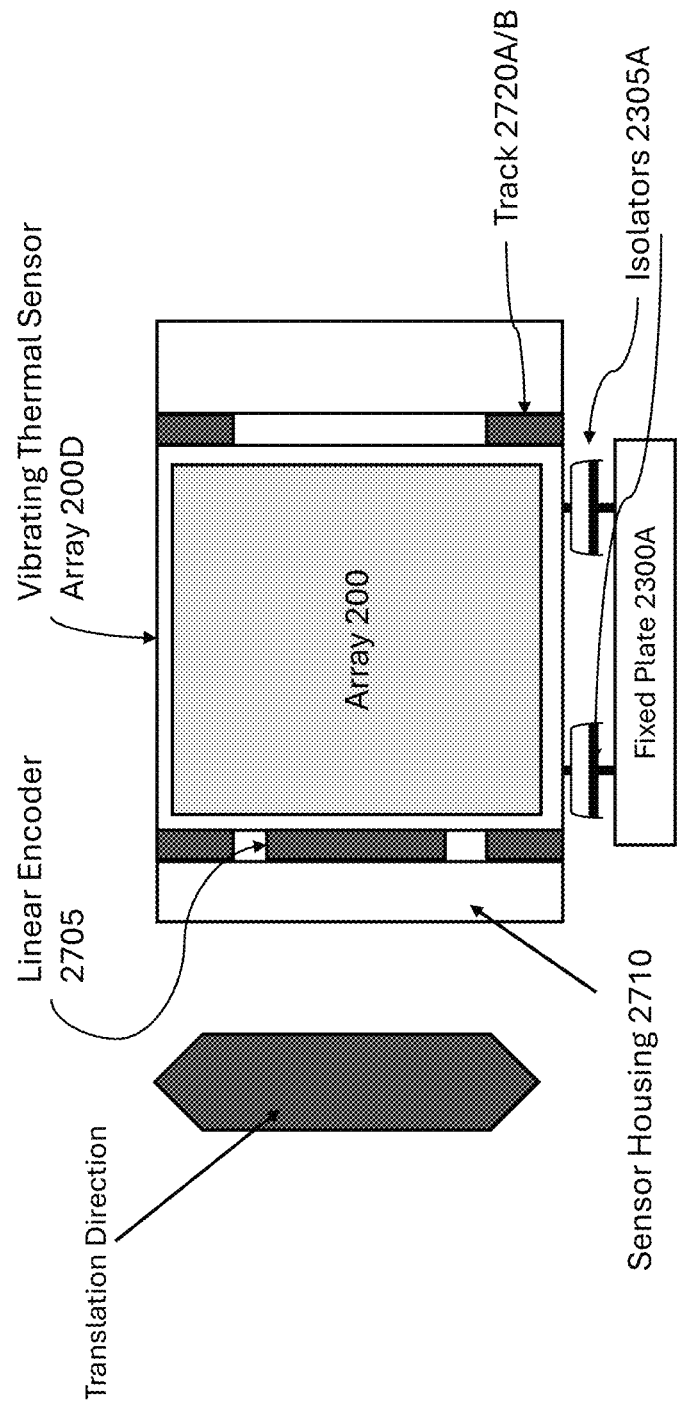
FIG. 33 depicts another example of an anti-detection mechanism in accordance with aspects of the disclosure.

FIG. 33 illustrates a view of an example of a vibrating thermal sensor array 200D in accordance with aspects of the disclosure. In this example, isolators 2305A are mounted on an end of the array 200. One end of the isolators 2305A is mounted to a fixed plate 2300A. This fixed plate 2300A may be mounted to the housing 600 of the system. Similar to the motorized thermal sensor array, the vibrating thermal sensor array 200D has a sensor housing 2710 with a fixed housing and a moveable housing and a track between them. The track may include bearings 2720A or slides 2720B. The vibrating thermal sensor array 200D also include a linear encoder 2705 used to determine the position of the array 200D (translation).

Figure 34:
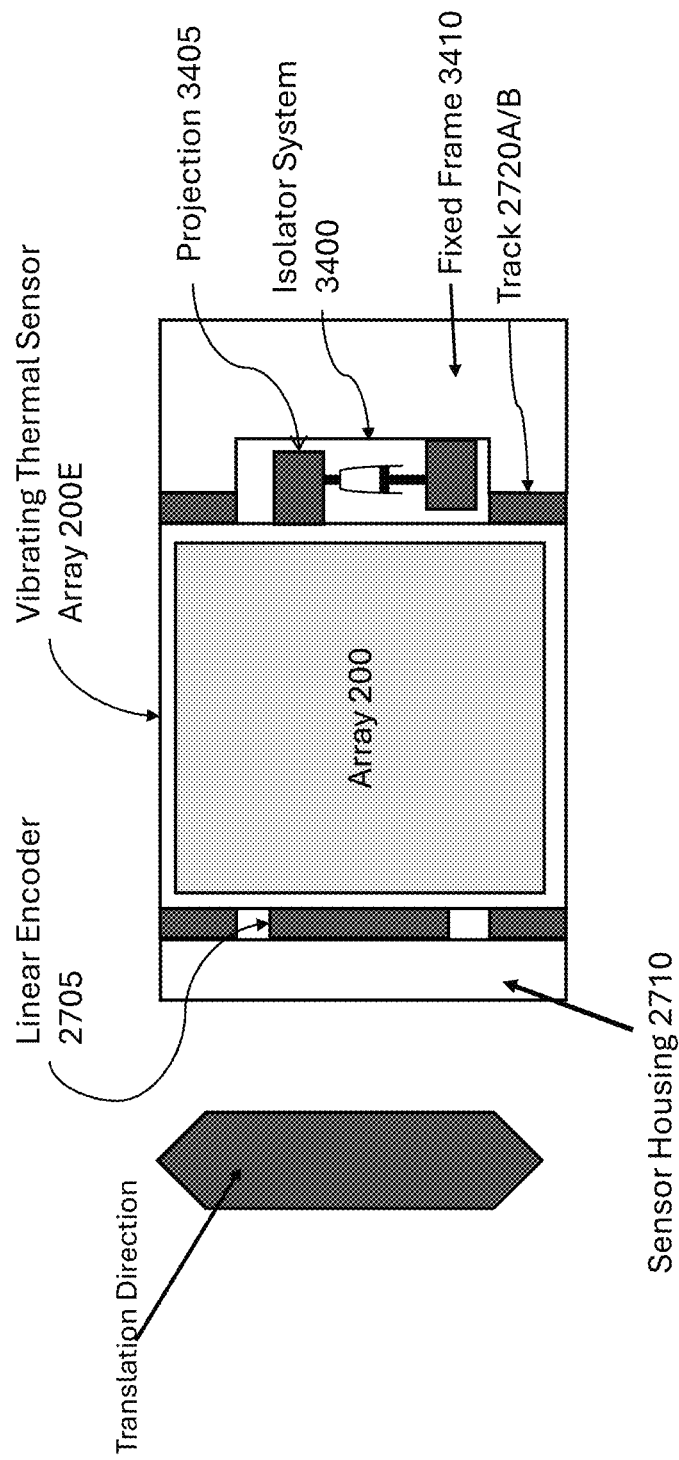
FIG. 34 depicts another example of an anti-detection mechanism in accordance with aspects of the disclosure.

In other aspects, one or more isolators may be mounted on one or more sides of the array as shown in FIG. 34. The isolator system 3400 in FIG. 34 includes one or more isolators. One end of the isolator(s) is mounted to a fixed frame 3400 and the other end is in contact with a projection 3405 from the moveable housing.

The isolator(s) may selected to achieve a maximum spreading of any emitted signal during readout but at the same time meet a blur requirement for the imaging.

As described above, an expected angular change over a time interval t is determine by equation 1.

Thus, the isolator 2305A may be selected such that $\phi$ is maximized at $\tau$ equal to the desired maximum integration time allowed to the detecting system but subject to a constraint that $\cancel{c}$ less than 1 pixel instantaneous field of view (IFOV) at $\tau$ equal to the sensor frame time.

In the linear translation case, the transfer function is equal to transmissibility function of the isolator and determines by $$H(j\omega)=T(j\omega) \qquad (6)$$

In an aspect of the disclosure, the selected isolator(s) 2305A may be based on the expected external stimulus. For example, there may be a different isolator where the system is handheld verses mounted on a vehicle.

In an aspect of the disclosure, the selected isolator 2305A may also be based on a desired maximum linear displacement over an expected external stimulus. This is because array 200D/200E is allowed to be translated without bound; too much of the field of view may be impacted.

In an aspect of the disclosure, the relationship between the translation of the array 200D/200E and the linear displacement of the image may be determined during calibration. For example, an external stimulus may be exerted on the system, the position of the array 200D/200E determined and the image translation may be determined, e.g., number of rows. This determined linear displacement may be stored in memory in a look up table. The process may be repeated for a plurality of times to generate multiple correspondences. Each being stored in the memory in the look up table.

In other aspects of the disclosure, the relationship may be determined arithmetically in a similar manner as described above.

Figure 35:
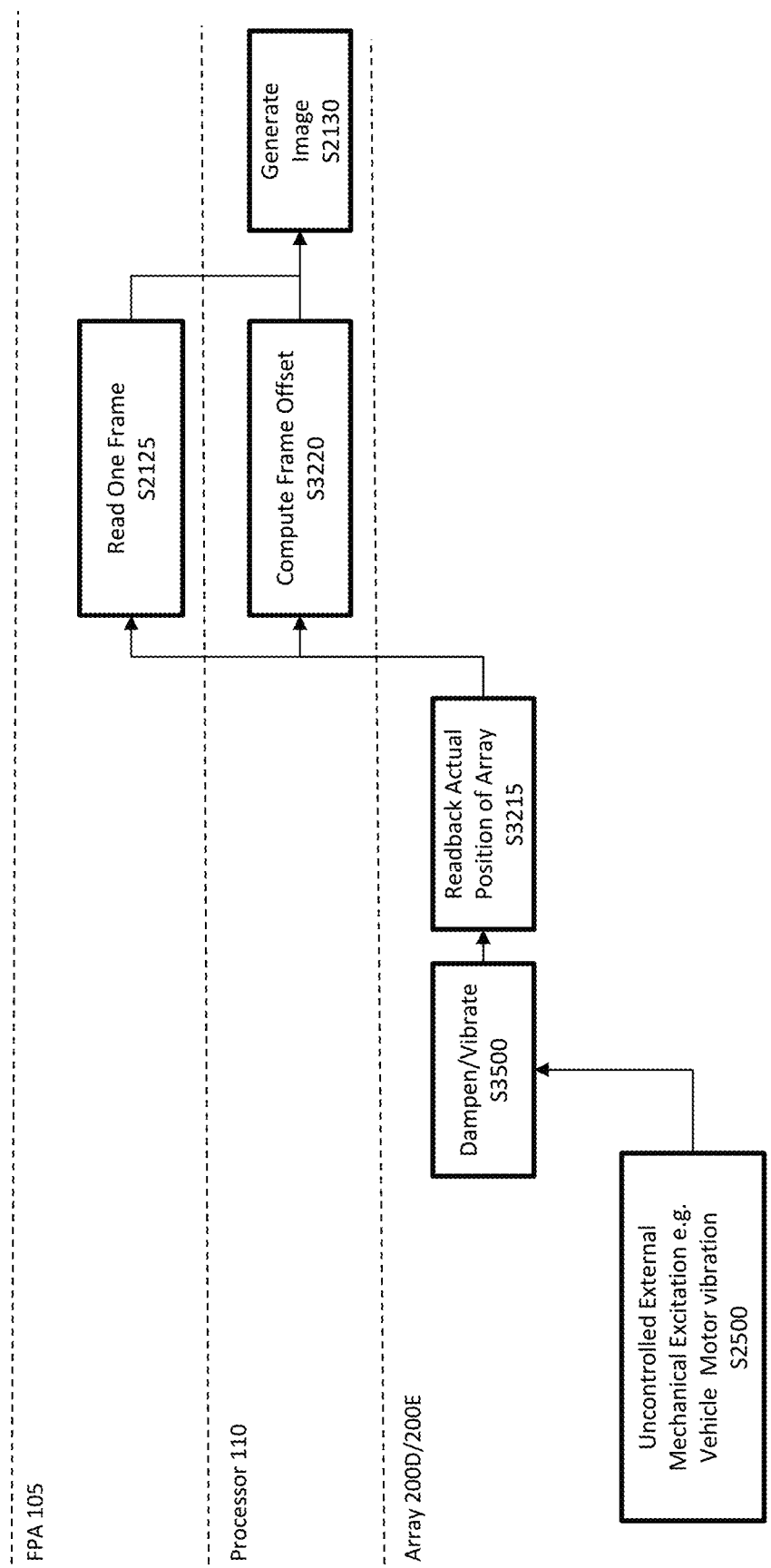
FIG. 35 depicts a flow for an anti-detection method in accordance with aspects of the disclosure.

FIG. 35 is a flow diagram of a method in accordance with aspects of the disclosure. At 2500, an external stimulus (mechanical excitation) is received by the system. As noted above, this stimulus may be due to a vehicle vibrating or a person moving. At S3500, the isolator(s) 2305A damping the vibrations and transfer the stimulus to the array 200D/200E.

When it is time to read one frame of the detection target 500, the processor 110 via the linear encoder 2705 determines the position of the array 200D/200E, e.g., amount of linear translation at S3215. This position may be the same as a prior position if no stimulus is applied. However, the position may change due to the stimulus and damping. In an aspect of the disclosure, the actual position may be determined periodically at the frame readout rate. In this aspect, just prior to issuing the frame command to the FPA 105, the processor 110 determines the position. In other aspects, the processor 110 may determine the position at the same time as issuing the frame command to the FPA 105 (e.g., in parallel). In other aspects of the disclosure, the processor 110 may determine the position when it receives the image data for a frame from the FPA 105.

At S3220, the processor 110 determines the linear displacement of the image using the determined position, e.g., frame offset. As described above, this determination may include using a look up table in memory. For example, the processor 110 may retrieve the look up table from memory and determine the line displacement, e.g., number of rows displaced, from the look up table, which corresponds to the determined position. The processor 110 issues frame command, row command(s) and current offsets for the row(s) to the FPA 105 (to the ROIC).

At 2125, the FPA 105 reads one frame of the detection target 500 and generates the image data for each row. In an aspect of the disclosure, the number of the rows within a frame that is readout may be different due to the rotation.

The FPA 105 (ROIC) transmits the image data for each row (commanded row) to the processor 110. At 2130, the processor 110 generates the image for display.

In an aspect of the disclosure, the size of the thermal sensor array may be larger than the size of the display for the image. For example, the thermal sensor array may have more rows than the display. The ratio of the thermal sensor array and display (number of rows more) may be determined by the maximum angular displacement (deflection) for the mirror face or maximum linear translation of the array 200D/200E such that the entire image of the detection target 500 may fit within the oversized thermal sensor array. In this aspect, the image data of the target may not be lost. For example, if the maximum angular displacement or linear translation moves the image +− 100 rows, the thermal sensor array may have two hundred more rows than the display. The processor 110 may translate the image data received from the FPA 150 using the determined offset for each frame such that the image is centered on the display.

In other aspects, even if the thermal sensor array is larger than the display, some of the detection target 500 may not be picked up when the mirror face is rotated to a maximum angular displacement (deflection) or maximum linear translation (background image data may be received instead). The processor 110 may translate the image data received from the FPA 150 using the determined offset. Additionally, the processor 110 may only generate an image for display where the row data is available for all of the frames.

FIG. 36 illustrates an example of image data for three frames. Between each frame either the mirror face is rotated or the array 200D/200E is moved. As can be seen, the image data is different for the different frames. The image is moved upward in frame N+1 (with respect to N frame) and downward in N+2 with respect to N (and N+1). If the detection target includes a person and tree, the detection target is completely viewed in frame N but not in N+1 and N+2.

For example, the edges of the image for frames may be removed when the same row does not appear in another frame such as shown in FIG. 37. The portions which may be removed are determined by the respective frame offsets determined above. As shown in FIG. 37, since the top of the tree is not shown in frame N+1, the top of the tree is not shown in the displayed image 3700.

In other aspects of the disclosure, the processor 110 may generate an image for display from the received image data by adding row image data from one or more of previous frames where row image data for the detection target is not contained in the current frame due to the rotation or linear translation. For example, if the rotation or linear translation resulted in a frame offset of 25 rows of image data, the processor 110 may retrieved from memory stored image data for the same 25 rows of the last frame and combine the retrieved 25 rows of image data with the image data received for the current frame. In other aspects, the processor 110 may retrieved from memory stored image data for the same rows, e.g., 25 of multiple previous frames and average the image data for each pixel, use the average image data and combine with the current image. FIG. 38 shows an example of a displayed image 3800 where data from a previous frame 3805 is combined to generate the displayed image 3800. In an aspect of the disclosure, the displayed image 3800 may also include an indication identifying that the displayed image contains image data from a previous frame. In an aspect of the disclosure, the image may be shaded in the region where the image data is from a previous frame.

In other aspects of the disclosure, the processor 110 may generate an image for display from the received image data by adding a predetermined image to the received image data where row image data of the detection target is not contained in the current frame due to the rotation or linear translation. The location of the predetermined image is based on the determined frame offset. The predetermined image may include an indication that image data is missing. The predetermined image may be a determined color such as a white image. FIG. 39 illustrates other example of a displayed image 3900 having a predetermined image 3905 in the region.

As described above, the relationship between rotation and number of rows may be determined using a look up table or calculation. In other aspects, the relationship may be determined using both a look up table and calculation. For example, the look up table may include a preset number of rotations/movement which may not include the actual determined position. Therefore, the processor 110 may interpolate the relationship by selecting the closest stored positions and interpolate the number of rows, e.g., frame offset.

What is claimed is:

1. A system comprising
a focal-plane array (FPA) comprising:
   a two-dimensional configuration of thermal sensors arranged in rows and columns; and
   readout circuitry to pulse bias one or more thermal sensors of one or more selected rows and obtain output from the pulse biased thermal sensors;
a shutter; and
a processor configured to control the shutter to interrupt an optical path between the pulse biased thermal sensors and an aperture of the system while the pulsed biased thermal sensors are being pulse biased, wherein the shutter comprises a plurality of alternating transparent and opaque sections coupled to a shaft and a motor, wherein the processor controls the position of these sections relative to the pulsed biased thermal sensors using the motor.

2. The system of claim 1, further comprises at least one focusing lens and relay optics, wherein at least a portion of the shutter is positioned at an intermediate focal plane.

3. The system of claim 1, further comprising an encoder configured to provide a location of the shaft to the processor, wherein the processor transmits a line synchronization signal to the readout circuitry based on the position of the shaft.

4. The system of claim 1, further comprising a memory having a correspondence table associating position of the shaft and corresponding row of the thermal sensors for readout.

5. The system of claim 1, wherein the shutter comprises a digital micromirror device (DMD).

6. The system of claim 5, wherein the processor is configured to control an angle of mirrors of the DMD to interrupt the optical path between the pulse biased thermal sensors and the aperture of the system while the pulse biased thermal sensors are pulse biased.

7. The system of claim 6, further comprising a beam dump, wherein while the pulsed biased thermal sensors are pulse biased, corresponding mirrors of the DMD are rotated such that emissions are reflected toward the beam dump.

8. The system of claim 7, further comprising a memory having a correspondence table associating the thermal sensors and corresponding mirrors, respectively, of the DMD.

9. The system of claim 7, wherein the beam dump is a portion of a housing of the system.

10. The system of claim 9, wherein the beam dump is made of a material which is absorptive to emissions of the thermal sensor array.

* * * * *